US011111296B2

(12) United States Patent
Thomas et al.

(10) Patent No.: US 11,111,296 B2
(45) Date of Patent: Sep. 7, 2021

(54) COMPOSITIONS AND METHODS FOR TREATING CARDIAC DYSFUNCTION

(71) Applicants: THE BROAD INSTITUTE, INC., Cambridge, MA (US); DANA-FARBER CANCER INSTITUTE, INC., Cambridge, MA (US)

(72) Inventors: David K. Thomas, Boston, MA (US); Todd R. Golub, Cambridge, MA (US)

(73) Assignees: THE BROAD INSTITUTE, INC., Cambridge, MA (US); DANA-FARBER CANCER INSTITUTE, INC., Cambridge, MA (US)

( * ) Notice: Subject to any disclaimer, the term of this patent is extended or adjusted under 35 U.S.C. 154(b) by 0 days.

(21) Appl. No.: 16/061,652

(22) PCT Filed: Dec. 13, 2016

(86) PCT No.: PCT/US2016/066390
§ 371 (c)(1),
(2) Date: Jun. 12, 2018

(87) PCT Pub. No.: WO2017/106196
PCT Pub. Date: Jun. 22, 2017

(65) Prior Publication Data
US 2018/0362647 A1    Dec. 20, 2018

Related U.S. Application Data

(60) Provisional application No. 62/267,158, filed on Dec. 14, 2015.

(51) Int. Cl.
| | |
|---|---|
| *G01N 33/48* | (2006.01) |
| *G01N 31/00* | (2006.01) |
| *C07K 16/28* | (2006.01) |
| *G16C 20/00* | (2019.01) |
| *G16C 10/00* | (2019.01) |
| *G16C 20/64* | (2019.01) |
| *G16C 20/50* | (2019.01) |
| *G16C 20/20* | (2019.01) |
| *G16C 20/62* | (2019.01) |
| *G16C 20/60* | (2019.01) |
| *A61P 9/10* | (2006.01) |
| *A61P 9/04* | (2006.01) |
| *A61K 39/00* | (2006.01) |
| *A61K 38/17* | (2006.01) |

(52) U.S. Cl.
CPC ............ *C07K 16/2803* (2013.01); *A61P 9/04* (2018.01); *A61P 9/10* (2018.01); *G16C 10/00* (2019.02); *G16C 20/00* (2019.02); *G16C 20/20* (2019.02); *G16C 20/50* (2019.02); *G16C 20/60* (2019.02); *G16C 20/62* (2019.02); *G16C 20/64* (2019.02); *A61K 38/1774* (2013.01); *A61K 2039/505* (2013.01); *C07K 2317/34* (2013.01)

(58) Field of Classification Search
None
See application file for complete search history.

(56) References Cited

U.S. PATENT DOCUMENTS

| | | |
|---|---|---|
| 5,385,740 A | 1/1995 | Tisdale et al. |
| 7,485,697 B2 | 2/2009 | Yamamoto et al. |
| 7,981,424 B2 | 7/2011 | Mjalli et al. |
| 8,420,083 B2 | 4/2013 | Strakhova et al. |
| 9,291,621 B2 | 3/2016 | Hahn et al. |
| 2003/0061198 A1 | 3/2003 | Itai et al. |
| 2003/0118592 A1 | 6/2003 | Ledbetter et al. |
| 2003/0133939 A1 | 7/2003 | Ledbetter et al. |
| 2003/0199561 A1 | 10/2003 | Adams et al. |
| 2004/0058445 A1 | 3/2004 | Ledbetter et al. |
| 2005/0136049 A1 | 6/2005 | Ledbetter et al. |
| 2005/0148536 A1 | 7/2005 | Greenberg |
| 2005/0175614 A1 | 8/2005 | Ledbetter et al. |
| 2005/0180970 A1 | 8/2005 | Ledbetter et al. |
| 2005/0186216 A1 | 8/2005 | Edbetter et al. |
| 2005/0202012 A1 | 9/2005 | Ledbetter et al. |
| 2005/0202023 A1 | 9/2005 | Ledbetter et al. |

(Continued)

FOREIGN PATENT DOCUMENTS

| | | |
|---|---|---|
| WO | 200104354 A2 | 1/2001 |
| WO | 2003064624 A2 | 8/2003 |

(Continued)

OTHER PUBLICATIONS

Verma, Neeraj, et al. "Structural and dynamic insights into S100B protein activity inhibition by melittin for the treatment of epilepsy." Int. J. Comp. App. NSAAILS 1 (2013): 55-60.*
Krishnan, Sreeram, et al. "A Molecular Dynamics Study on RAGE-Aβ42 Interaction and the Influence of G82S RAGE Polymorphism on Aβ Interaction." International Journal Bioautomation 19.4 (2015).*
Chaney, Michael O., et al. "RAGE and amyloid beta interactions: atomic force microscopy and molecular modeling." Biochimica et Biophysica Acta (BBA)-Molecular Basis of Disease 1741.1-2 (2005): 199-205.*
Serratos, Iris N., et al. "Modeling the interaction between quinolinate and the receptor for advanced glycation end products (RAGE): relevance for early neuropathological processes." PLoS One 10.3 (2015): pp. 1-22.*

(Continued)

*Primary Examiner* — Anna Skibinsky
(74) *Attorney, Agent, or Firm* — Greenberg Traurig, LLP; Melissa Hunter-Ensor; Kristopher Reichlen

(57) ABSTRACT

The invention provides compositions and methods for treating cardiac dysfunction, particularly cachexia-associated or RAGE-associated cardiac dysfunction, using an anti-RAGE agent. The invention also provides compositions and methods for identifying therapeutic agents useful for disrupting (slowing, reducing, reversing, or preventing). The methods comprise designing or identifying agents that bind to functional sites identified on the RAGE polypeptide, wherein binding of agents to the functional site(s) inhibit RAGE-mediated cachetogenic signaling.

7 Claims, 23 Drawing Sheets

Specification includes a Sequence Listing.

(56) References Cited

U.S. PATENT DOCUMENTS

| | | |
|---|---|---|
| 2005/0202028 A1 | 9/2005 | Ledbetter et al. |
| 2005/0202534 A1 | 9/2005 | Ledbetter et al. |
| 2005/0238646 A1 | 10/2005 | Ledbetter et al. |
| 2007/0286858 A1 | 12/2007 | Clancy et al. |
| 2009/0270480 A1 | 10/2009 | Amegadzie et al. |
| 2010/0151589 A1 | 6/2010 | Tisdale et al. |
| 2010/0226915 A1 | 9/2010 | Hahn et al. |
| 2010/0254983 A1* | 10/2010 | Schmidt ................ A61P 3/04 424/134.1 |
| 2012/0196828 A1 | 8/2012 | Marcus |
| 2013/0078728 A1 | 3/2013 | Li et al. |
| 2013/0269046 A1 | 10/2013 | Kinsella et al. |
| 2016/0305934 A1* | 10/2016 | Thomas ............... A61K 31/506 |
| 2017/0015996 A1* | 1/2017 | Croce ................ A61K 31/711 |
| 2017/0240632 A1 | 8/2017 | Thomas et al. |
| 2018/0355033 A1 | 12/2018 | Thomas et al. |
| 2019/0195862 A1 | 6/2019 | Thomas et al. |

FOREIGN PATENT DOCUMENTS

| | | |
|---|---|---|
| WO | 2004016229 A2 | 2/2004 |
| WO | 2004045617 A1 | 6/2004 |
| WO | 2006012415 A2 | 2/2006 |
| WO | 2007/089616 A2 | 8/2007 |
| WO | 2007109747 A2 | 9/2007 |
| WO | 2007109749 A2 | 9/2007 |
| WO | 2008137552 A2 | 11/2008 |
| WO | 2009136382 A2 | 11/2009 |
| WO | 2011042548 A1 | 4/2011 |
| WO | 2011053707 A1 | 5/2011 |
| WO | 2015085097 A1 | 6/2015 |
| WO | 2016061532 A1 | 4/2016 |
| WO | 2016/201319 A1 | 12/2016 |
| WO | 2016201368 A1 | 12/2016 |

OTHER PUBLICATIONS

Han, Young Taek, et al. "Ligand-based design, synthesis, and biological evaluation of 2-aminopyrimidines, a novel series of receptor for advanced glycation end products (RAGE) inhibitors." Journal of medicinal chemistry 55.21 (2012): 9120-9135.*

Brederson et al., "A Monoclonal Antibody Against the Receptor for Advanced Glycation End Products Attenuates Inflammatory and Neuropathic Pain in the Mouse", European Journal of Pain, vol. 20, Sep. 22, 2015, pp. 3077-614, ISSN: 1532-2149, DOI: https://doi.org/10.1002/ejp.775.

Deane et al., "A Multimodal RAGE-Specific Inhibitor Reduces Amyloid [beta]-Mediated Brain Disorder in a Mouse Model of Alzheimer Disease", Journal of Clinical Investigation, vol. 122, No. 4, Apr. 2, 2012, pp. 1377-1392, ISSN: 0021-9738, DOI: 10.1172/JCI58642.

Yan et al., "Effects of Advanced Glycation End Products on Calcium Handling in Cardiomyocytes", Cardiology, vol. 129, No. 2, Jan. 1, 2014, pp. 75-83, ISSN: 0008-6312, DOI: 10.1159/000364779.

Extended European Search Report, dated May 15, 2019, received in corresponding European Application No. 16876492.6 (10 pages).

Yatime, L. et al., "Structural Insights Into the Oligomerization Mode of the Human Receptor for Advanced Glycation End-Products," Febs Journal, vol. 280, No. 24, pp. 6556-6568 (2013).

International Search Report and Written Opinion for Corresponding PCT Patent Application No. PCT/US2016/066390, dated Mar. 17, 2017 (10 pages).

Acharyya et al., "Cancer cachexia is regulated by selective targeting of skeletal muscle gene products," The Journal of Clinical Investigation, Aug. 2004, vol. 114, No. 3, pp. 370-378 (9 pages).

Arumugam et al., "S100P-Derived RAGE Antagonistic Peptide (RAP) Reduces Tumor Growth and Metastasis," Clinical Cancer Research, Aug. 2012, vol. 18, Iss. 16; DOI: 10.1158/1078-0432.CCR-12-0221 (20 pages).

Azeliragon, PF-04494700, Product Data Sheet, MedChemExpress, downloaded from the Internet on Jun. 10, 2020 (2 pages).

Boehm et al., "Towards systematic functional characterization of cancer genomes," Nature Reviews Genetics, Jul. 2011, vol. 12, Iss. 7, pp. 487-498 (12 pages).

Certificate of Analysis, Product Name: "FPS ZM1," TOCRIS, Sep. 5, 2017 (2 pages).

Das et al., "The role of triglyceride lipases in cancer associated cachexia," Trends in Molecular Medicine, May 1, 2013, vol. 19, No. 5, pp. 292-301 (10 pages).

Ebner et al., "Mechanism and novel therapeutic approaches to wasting in chronic disease," Maturitas, May 9, 2013, vol. 75, No. 3, pp. 199-206 (8 pages).

Fearon et al., "Understanding the mechanisms and treatment options in cancer cachexia," Nature Reviews Clinical Oncology, 2013, vol. 10, No. 2, pp. 90-99 (10 pages).

Krepinsky et al., "Developments in mitogen-induced extracellular kinase 1 inhibitors and their use in the treatment of disease," Expert Opinion on Therapeutic Patents, 2002, vol. 12, No. 12, pp. 1795-1811 (17 pages).

Murphy et al., "Physiological characterization of a mouse model of cachexia in colorectal liver metastases," American Journal of Physiology: Regulatory, Integrative and Comparative Physiology, May 15, 2013, vol. 304, No. 10, pp. R854-R864 (11 pages).

Neeper et al., "Cloning and Expression of a Cell Surface Receptor for Advanced Glycosylation End Products of Proteins," The Journal of Biological Chemistry, 1992, vol. 267, No. 21, pp. 14998-15004 (7 pages).

Nerurkar et al., "*Momordica charantia* (bitter melon) inhibits primary human adipocyte differentiation by modulating adipogenic genes," Complementary and Alternative Medicine, Jun. 29, 2013, vol. 10, No. 34, pp. 1-10 (10 pages).

Ort et al., "Recombinant Human FIZZ3/Resistin Stimulates Lipolysis in Cultured Human Adipocytes, Mouse Adipose Explants, and Normal Mice," Endocrinology, Feb. 10, 2005, vol. 146, No. 5, pp. 2200-2209 (10 pages).

Penna et al., "Muscle Wasting and Impaired Myogenesis in Tumor Bearing Mice are Prevented by ERK Inhibition," Plos One, Oct. 27, 2010, vol. 5, No. 10, e13604, pp. 1-11 (11 pages).

Prado et al., "Skeletal muscle anabolism is a side effect of therapy with the MEK inhibitor selumetinib in patients with cholangiocarcinoma," British Journal of Cancer, 2012, vol. 106, No. 10, pp. 1583-1586 (4 pages).

Sabbagh et al., "PF-04494700, an Oral Inhibitor of Receptor for Advanced Glycation End Products (RAGE), in Alzheimer's disease," Alzheimer Disease and Associated Disorders, 2011, vol. 25, Iss. 3, pp. 206-212 (14 pages).

Salama et al., "A review of the S100 proteins in cancer," European Journal of Surgical Oncology, 2008, vol. 34, No. 4, pp. 357-364. (Abstract, 2 pages).

Scott et al., "Large-scale isolation of human skeletal muscle satellite cells from post-mortem tissue and development of quantitative assays to evaluate modulators of myogenesis," Journal of Cachexia, Sarcopenia, and Muscle, Jun. 1, 2013, vol. 4, pp. 157-169 (26 pages).

Yao et al., "Expression of S100 Protein Family Members in the Pathogenesis of Bladder Tumors," Anticancer Research, 2007, vol. 27, pp. 3051-3058 (9 pages).

Zhou et al., "Reversal of Cancer Cachexia and Muscle Wasting by ActRIIB Antagonism Leads to Prolonged Survival," Cell, Aug. 2010, vol. 142, Iss. 4, pp. 531-543 (13 pages).

Communication pursuant to Rules 70(2) and 70a(2) EPC in European Patent Application No. 14868683.5, dated Aug. 1, 2017 (1 page).

European Examination Report in European Patent Application No. 14868683.5, dated Apr. 18, 2018 (5 pages).

Examination Report issued in corresponding. European Patent Application No. 16876492.6, dated May 28, 2020 (7 pages).

Extended European Search Report in European Patent Application No. 14868683.5, dated Jul. 14, 2017 (17 pages).

International Search Report and Written Opinion in International Patent Application No. PCT/US2014/068631, dated Mar. 30, 2015 (17 pages).

Partial European Search Report in European Patent Application No. 19189695.0, dated Feb. 28, 2020 (15 pages).

(56) References Cited

OTHER PUBLICATIONS

Partial Supplementary European Search Report in European Patent Application No. 14868683.5, dated Apr. 7, 2017 (11 pages).

* cited by examiner

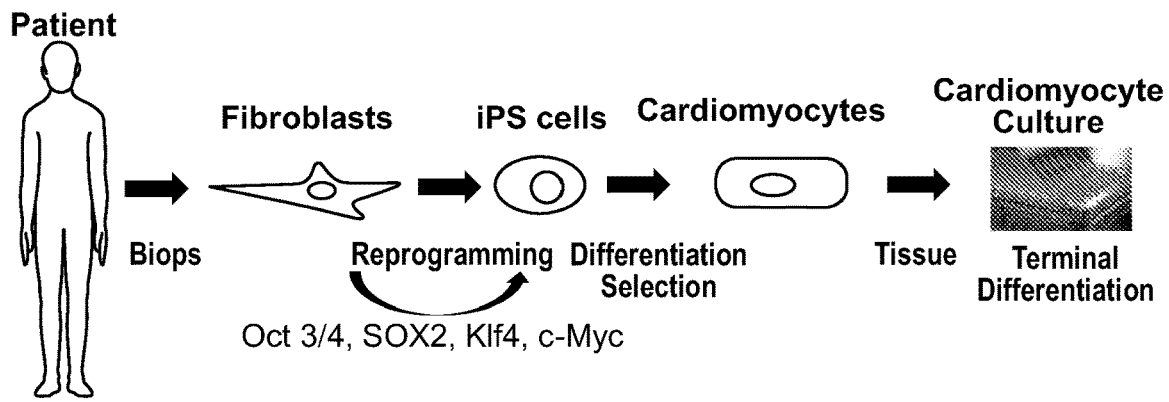
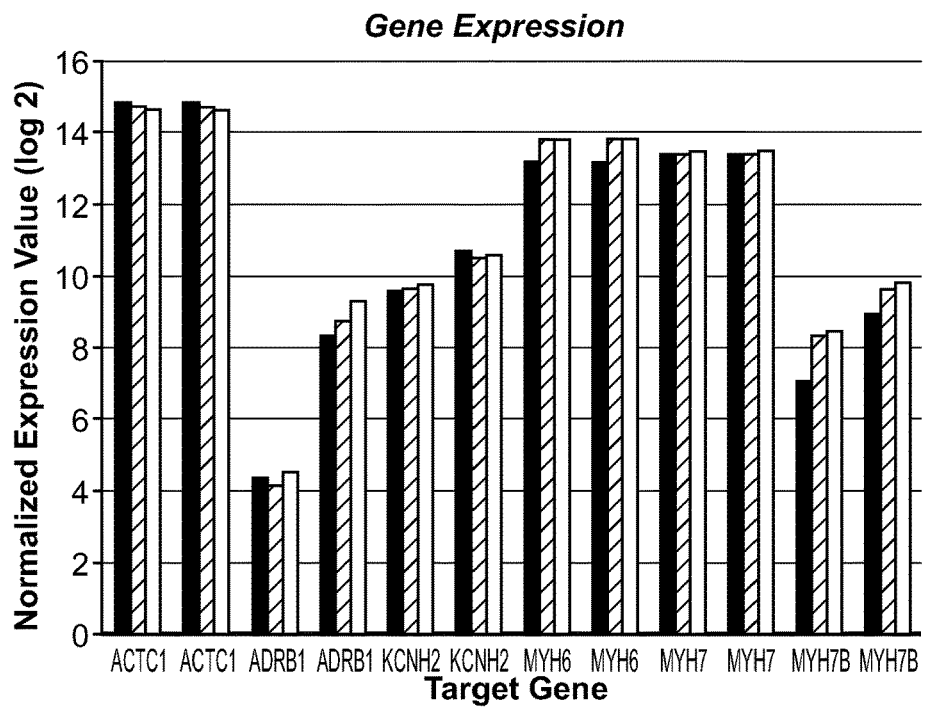
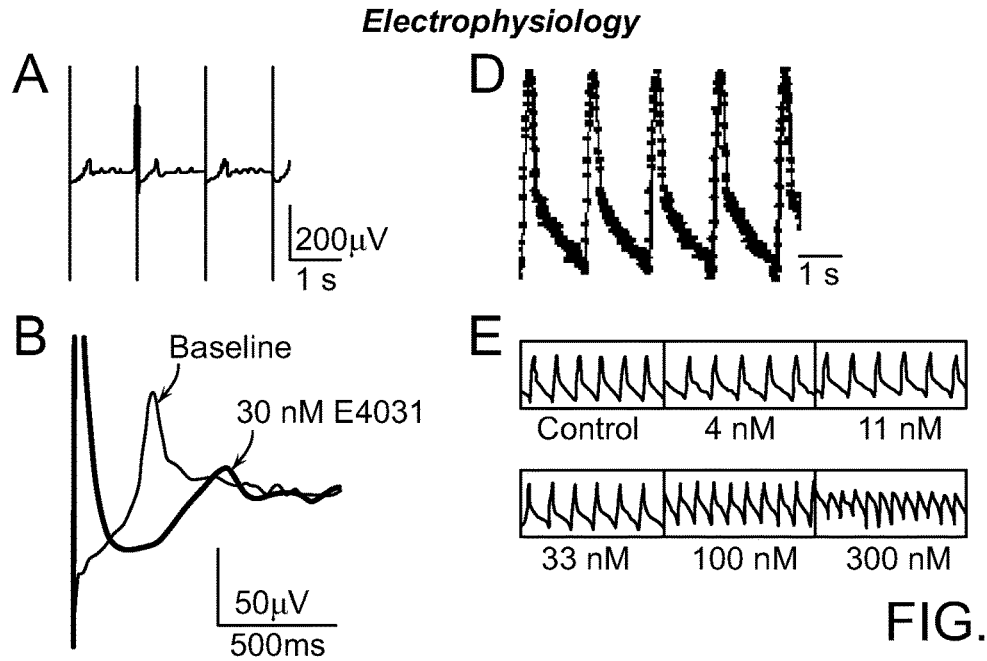
FIG. 13

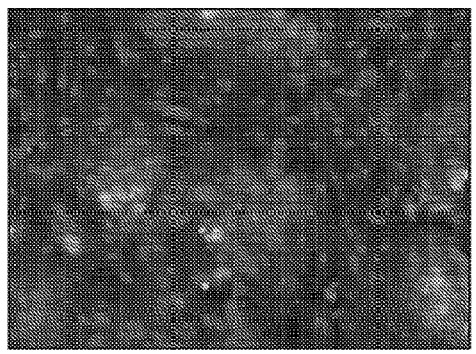
Inducing CM + RAGE Ab *Rescue*
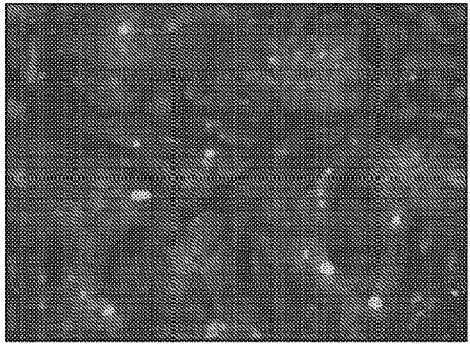
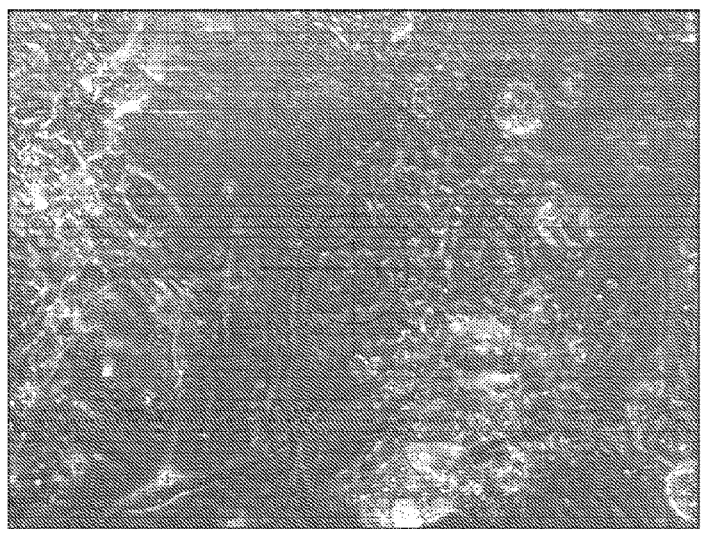
*Rescue*: 3D Inducing CM, followed by 3D Inducing CM + RAGE Ab
FIG. 16

16 of 22 anti-mouse RAGE Abs cross react with human < 2e^-07 = 73%
Anti-RAGE antibodies from flock immunization NB = no binding

| Antibody | mg/mL | % Monomer | Endotoxin EU/mg | Isotype | EC50 (nM) mRAGE (direct ELISA) | Kd (nM) mRAGE | Kd (nM) hRAGE | Binding site | Aliquot size |
|---|---|---|---|---|---|---|---|---|---|
| A | 0.31 | 80.53 | 0.65 | rat IgG1/K | 0.95 | 1.3E-10 | NB | V+C1 domain | 100 ug |
| B | 1.56 | 96.46 | 0.1 | rat IgG1/K | 0.58 | 1.8E-09 | 1.50E-09 | V+C1 domain | 1 mg |
| C | 0.68 | 94.74 | 1.11 | rat IgG1/K | 1.01 | 7.6E-11 | 7.90E-09 | V+C1 domain | 100 ug |
| D | 1.12 | 100 | 0.11 | rat IgG2a/K | 0.08 | 8.4E-10 | 1.90E-07 | C2 domain | 1 mg |
| E* | 1.97 | 89.31 | 1.06 | rat IgG2a/K | 17.27 | NB | NB | V+C1 domain | 1 mg |
| F | 2.06 | 91.8 | 0.66 | rat IgG1/K | 0.56 | 2.0E-10 | NB | V+C1 domain | 1 mg |
| G | 1.97 | 90.72 | 0.63 | rat IgG2a/K | 0.09 | 4.4E-09 | 9.90E-09 | C2 domain | 1 mg |
| H | 2.25 | 97.34 | 0.18 | rat IgG1/K | 0.45 | 1.4E-08 | 8.90E-09 | C2 domain | 1 mg |

*Antibody E did not bind human and mouse RAGE in Biacore, but bound mRAGE in direct ELISA Anti-RAGE antibodies from cDNA immunization

| Antibody | mg/mL | % Monomer | Endotoxin EU/mg | Isotype | EC50 (nM) mRAGE (direct ELISA) | Kd (nM) mRAGE | Kd (nM) hRAGE | Binding site | Aliquot size |
|---|---|---|---|---|---|---|---|---|---|
| K | 0.85 | 100 | 0.87 | IgG2a/K | 0.16 | 6.1E-11 | 2.3E-10 | V+C1 | 100 ug |
| L | 1.15 | 100 | 0.79 | IgG2a/K | 0.09 | 2.0E-10 | 8.6E-10 | V+C1 | 100 ug |
| M | 1.18 | 99.92 | 0.43 | IgG2a/K | 0.06 | 1.1E-10 | 5.1E-10 | V+C1 | 100 ug |
| N | 1.01 | 98.78 | 0.24 | IgG2b/K | 0.29 | 2.3E-10 | 3.8E-10 | V+C1 | 1 mg |
| O | 0.94 | 100 | 0.22 | IgG2a/K | 0.10 | 2.5E-11 | NB | V+C1 | 100 ug |
| P | 1.04 | 100 | 0.41 | IgG2a/K | 0.06 | 1.6E-10 | 7.1E-10 | V+C1 | 1 mg |
| Q | 0.83 | 98.86 | 1.14 | IgG2a/K | 0.10 | 2.0E-11 | NB | V+C1 | 100 ug |
| R | 1.81 | 99.98 | 0.79 | IgG2a/K | 0.06 | 1.6E-10 | 9.8E-10 | V+C1 | 1 mg |
| S | 0.8 | 100 | 0.31 | IgG2a/K | 0.07 | 1.1E-10 | 5.0E-10 | V+C1 | 100 ug |
| T | 1.26 | 99.73 | 0.12 | IgG2a/K | 0.03 | 1.8E-11 | 3.5E-07 | V+C1 | 100 ug |
| U | 1.56 | 97 | 0.05 | IgG2a/K | 0.10 | 9.1E-11 | 8.4E-10 | V+C1 | 1 mg |
| V | 1.15 | 94.68 | 0.29 | IgG2a/K | 0.11 | 1.8E-11 | NB | V+C1 | 1 mg |
| W | 2.02 | 100 | 0.22 | IgG2a/K | 0.05 | 5.5E-11 | NB | V+C1 | 1 mg |
| X | 1.08 | 97.97 | 0.51 | IgG1/K | 0.29 | 1.4E-10 | 1.8E-09 | V+C1 | 1 mg |

FIG. 19

16 of 22 anti-mouse RAGE Abs cross react with human < 2e^-07 = 73%

Anti-RAGE antibodies from Hock immunization    NB = no binding

| Antibody | mg/mL | % Monomer | Endotoxin EU/mg | Isotype | EC50 (nM) mRAGE (direct ELISA) | Kd (nM) mRAGE | Kd (nM) hRAGE | Binding site | Aliquot size | Inhibitory mouse Cxa Assay | Inhibitory human Cxa Assay |
|---|---|---|---|---|---|---|---|---|---|---|---|
| A | 0.31 | 80.53 | 0.65 | rat IgG1/K | 0.95 | 1.3E-10 | NB | V+C1 domain | 100 ug | X | X |
| B | 1.56 | 96.46 | 0.1 | rat IgG1/K | 0.58 | 1.8E-09 | 1.50E-09 | V+C1 domain | 1 mg | X | X |
| C | 0.68 | 94.74 | 1.11 | rat IgG1/K | 1.01 | 7.6E-11 | 7.90E-09 | V+C1 domain | 100 ug | X | X |
| D | 1.12 | 100 | 0.11 | rat IgG2a/K | 0.08 | 8.4E-10 | 1.90E-07 | C2 domain | 1 mg | ++ | ++ |
| E* | 1.97 | 89.31 | 1.06 | rat IgG2a/K | 17.27 | NB | NB | V+C1 domain | 1 mg | X | X |
| F* | 2.06 | 91.8 | 0.66 | rat IgG1/K | 0.56 | 2.0E-10 | NB | V+C1 domain | 1 mg | X | X |
| G | 1.97 | 90.72 | 0.63 | rat IgG2a/K | 0.09 | 4.4E-09 | 9.90E-09 | C2 domain | 1 mg | X | X |
| H | 2.25 | 97.34 | 0.18 | rat IgG1/K | 0.45 | 1.4E-08 | 8.90E-09 | C2 domain | 1 mg | X | X |

*Antibody E did not bind human and mouse RAGE in Biacore, but bound mRAGE in direct ELISA
*Has limited inhibitory activity (HSkM > MSkM)

Anti-RAGE antibodies from cDNA immunization

| Antibody | mg/mL | % Monomer | Endotoxin EU/mg | Isotype | EC50 (nM) mRAGE (direct ELISA) | Kd (nM) mRAGE | Kd (nM) hRAGE | Binding site | Aliquot size | Inhibitory mouse Cxa Assay | Inhibitory human Cxa Assay |
|---|---|---|---|---|---|---|---|---|---|---|---|
| K | 0.85 | 100 | 0.87 | IgG2a/K | 0.16 | 6.1E-11 | 2.3E-10 | V+C1 | 100 ug | X | X |
| L | 1.15 | 100 | 0.79 | IgG2a/K | 0.09 | 2.0E-10 | 8.6E-10 | V+C1 | 100 ug | X | X |
| M | 1.18 | 99.92 | 0.43 | IgG2a/K | 0.06 | 1.1E-10 | 5.1E-10 | V+C1 | 100 ug | X | X |
| N | 1.01 | 98.78 | 0.24 | IgG2b/K | 0.29 | 2.3E-10 | 3.8E-10 | V+C1 | 1 mg | X | X |
| O | 0.94 | 100 | 0.22 | IgG2a/K | 0.10 | 2.5E-11 | NB | V+C1 | 100 ug | X | X |
| Q | 1.04 | 100 | 0.41 | IgG2a/K | 0.06 | 1.6E-10 | 7.1E-10 | V+C1 | 1 mg | X | X |
| R | 0.83 | 98.86 | 1.14 | IgG2a/K | 0.10 | 2.0E-11 | NB | V+C1 | 100 ug | X | X |
| S | 1.81 | 99.98 | 0.79 | IgG2a/K | 0.06 | 1.6E-10 | 9.8E-10 | V+C1 | 1 mg | X | X |
| T | 0.8 | 100 | 0.31 | IgG2a/K | 0.07 | 1.1E-10 | 5.0E-10 | V+C1 | 100 ug | X | X |
| U | 1.26 | 99.73 | 0.12 | IgG2a/K | 0.03 | 1.8E-11 | 3.5E-07 | V+C1 | 100 ug | X | X |
| | 1.56 | 97 | 0.05 | IgG2a/K | 0.10 | 9.1E-11 | 8.4E-10 | V+C1 | 1 mg | X | X |
| V | 1.15 | 94.68 | 0.29 | IgG2a/K | 0.11 | 1.8E-11 | NB | V+C1 | 1 mg | X | X |
| | 2.02 | 100 | 0.22 | IgG2a/K | 0.05 | 5.5E-11 | NB | V+C1 | 1 mg | X | X |
| X | 1.08 | 97.97 | 0.51 | IgG1/K | 0.29 | 1.4E-10 | 1.8E-09 | V+C1 | 1 mg | +++ | +++ |

FIG. 22

COMPOSITIONS AND METHODS FOR TREATING CARDIAC DYSFUNCTION

CROSS-REFERENCE TO RELATED APPLICATION

This application is the U.S. national phase application, pursuant to 35 U.S.C. § 371, of PCT International Application Ser. No.: PCT/US2016/066390, filed Dec. 13, 2016, designating the United States and published in English, which claims the benefit of the following U.S. Provisional Application No. 62/267,158, filed Dec. 14, 2015, the entire content of which is incorporated herein by reference.

STATEMENT OF RIGHTS TO INVENTIONS MADE UNDER FEDERALLY SPONSORED RESEARCH

This invention was made with government support under Grant. No. R01CA190101-01 awarded by the National Institutes of Health. The government has certain rights in the invention.

BACKGROUND OF THE INVENTION

Cardiac disease or cardiac dysfunction remains a global health problem. Advanced glycation end products and the receptor for advanced glycation end products (RAGE) have been implicated in cardiac disease. Diseases such as heart dysfunction or heart failure can also be associated with cachexia. The pathogenesis of cardiac dysfunction associated with RAGE or cachexia is not currently well-understood.

Accordingly, compositions and methods for treating cardiac dysfunction, such as cardiac dysfunction associated with RAGE and/or cachexia, are urgently required. Further, methods for identifying therapeutic agents having cardiac dysfunction-inhibiting or cachexia-inhibiting activity are urgently needed.

SUMMARY OF THE INVENTION

The invention generally provides compositions and methods of inhibiting, preventing, or reversing cardiac dysfunction, methods of identifying therapeutic agents useful for disrupting (slowing, reducing, reversing, or preventing) cachectic signaling in cells by targeting functional sites on RAGE polypeptide and/or cachectogenic ligands of RAGE, and therapeutic agents identified using the methods.

In one aspect, the invention provides a pharmaceutical composition that contains an effective amount of an agent that specifically binds to a RAGE polypeptide at a site containing one or more of the amino acid residues 25, 54, 59, 61, 91, 92, 94, 96, 98, 114, 116, 150, 151, 152, 154, 175, 177, 178, 179, 186, 213, 214, and 216 of the RAGE polypeptide, and a pharmaceutically acceptable excipient.

In another aspect, the invention provides a pharmaceutical composition that contains an effective amount of an agent that inhibits binding of a RAGE ligand to a RAGE polypeptide at a site containing one or more of the amino acid residues 25, 54, 59, 61, 91, 92, 94, 96, 98, 114, 116, 150, 151, 152, 154, 175, 177, 178, 179, 186, 213, and 216 of the RAGE polypeptide, and a pharmaceutically acceptable excipient.

In various embodiments of any one of the aspects delineated herein, the agent is an antibody or antigen binding fragment thereof, peptide, polynucleotide, or small molecule compound. In various embodiments, the RAGE ligand is S100A7, S100A8, or S100A9. In some embodiments, the agent binds at a site containing one or more of amino acid residues 23-54 of the RAGE polypeptide. In some other embodiments, the site contains each of amino acid residues 25, 54, 59, 61, 92, 94, 96, 114, 116, 150, 151, 152, 175, 177, 179, 186, and 214 of the RAGE polypeptide.

In various embodiments, an effective amount is an amount sufficient to inhibit loss of myosin heavy chain in a cell contacted with the composition. In some other embodiments, an effective amount is an amount sufficient to inhibit cachexia-associated cardiac dysfunction in a subject administered with the composition.

In yet another aspect, the invention provides a method of inhibiting loss of myosin heavy chain in a cardiomyocyte. The method contains the step of contacting the cardiomyocyte with an effective amount of an agent that specifically binds to a RAGE polypeptide, thereby inhibiting loss of myosin heavy chain in the cardiomyocyte.

In still another aspect, the invention provides a method of reversing loss of myosin heavy chain in a cardiomyocyte, the method containing the step of contacting the cardiomyocyte with an effective amount of an agent that specifically binds to a RAGE polypeptide, thereby reversing loss of myosin heavy chain in the cardiomyocyte. In some embodiments, the cardiomyocyte is in vivo or in vitro.

In another aspect, the invention provides a method of preventing and/or inhibiting cardiac dysfunction in a subject, the method containing the step of administering to the subject an effective amount of an agent that specifically binds to a RAGE polypeptide, thereby preventing or inhibiting cardiac dysfunction in the subject.

In yet another aspect, the invention provides a method of reversing cardiac dysfunction in a subject. The method contains the step of administering to the subject an effective amount of an agent that specifically binds to a RAGE polypeptide, thereby reversing cardiac dysfunction in the subject.

In still another aspect, the invention provides a method of treating cardiac dysfunction in a subject. The method contains the step of administering to the subject an effective amount of an agent that specifically binds to a RAGE polypeptide, thereby treating cardiac dysfunction in the subject.

In another aspect, the invention provides a method of treating cardiac dysfunction in a selected subject. The method contains the step of administering to the subject an effective amount of an agent that specifically binds to a RAGE polypeptide, where the subject is selected as having an increased level of S100A7, S100A8, or S100A9 polypeptide or polynucleotide in a biological sample obtained from the subject relative to a control level, thereby treating cardiac dysfunction in the subject.

In various embodiments of any one of the aspects delineated herein, the subject is human. In some embodiments, the cardiac dysfunction is cachexia-associated cardiac dysfunction. In some other embodiments, the cardiac dysfunction is heart dysfunction associated with cancer cachexia, cachexia-associated advanced heart failure, heart dysfunction following acute myocardial infarction, cardiac ischemia, or cardiac atrophy.

In some embodiments, the agent is FPS3. In some other embodiments, the agent is an anti-RAGE antibody.

In another aspect, the invention provides a method for identifying a candidate compound that binds to a site on a RAGE polypeptide. The method contains the steps of (a) providing a three-dimensional structure of a RAGE polypeptide having at least one atomic coordinate, or surrogate thereof, from PDB ID: 4LP4 for each of the amino acid residues 23-54 or for each of the amino acid residues 25, 54, 59, 61, 91, 92, 94, 96, 98, 114, 116, 150, 151, 152, 154, 175, 177, 178, 179, 186, 213, and 216 of the RAGE polypeptide: or atomic coordinates that have a root mean square deviation of the coordinates of less than 3 angstroms; and (b) producing a structure for a candidate compound wherein the structure defines a molecule having sufficient surface complementary to the RAGE polypeptide to bind the site in an aqueous solution.

In various embodiments, the method further contains the step of (c) evaluating the ability of the compound to bind a RAGE polypeptide in an in vitro, in vivo, or ex vivo assay. In some embodiments, the method further contains the step of (d) evaluating the ability of the compound to inhibit cachexia or inhibit loss of myosin heavy chain in a functional assay. In some other embodiments, the method contains the step of (e) modifying the candidate compound based upon the positioning, alignment, and interactions between the candidate compound and one or more amino acids in the site. In some embodiments, the structure of the candidate compound is designed de novo. In still other embodiments, the results of the evaluation in step (c) or step (d) provide further structure related binding information such that other candidate compounds are selected for evaluation in step (c) or step (d).

Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant a peptide, nucleic acid molecule, or small compound.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels.

As used herein, an "anti-RAGE agent" or "RAGE inhibitor" is an agent that inhibits a biological activity or function of RAGE. Exemplary biological activities of RAGE include, without limitation, binding to advanced glycation end products (AGEs), amyloid fibrils, amphoterins, and S100/calgranulins, such as S100A7, S100A8, and S100A9. In particular embodiments, the biological activity or function of RAGE is RAGE-mediated cachectogenic signaling. In some embodiments, the anti-RAGE agent is an anti-RAGE antibody, or antigen-binding fragment thereof, having cachexia-inhibitory activity. In some other embodiments, the anti-RAGE agent is an anti-S100A7, anti-S100A8, or anti-S100A9 antibody, or antigen-binding fragment thereof, having cachexia-inhibitory activity. In still other embodiments, the anti-RAGE agent is a small molecular compound binding to RAGE and having cachexia-inhibitory activity. In some embodiments, the anti-RAGE agent is FPS3.

Exemplary RAGE inhibitors include, without limitation, PF-04494700 (also known as TTP-488) (Sabbagh et al., Alzheimer Dis Assoc Disord. 2011; 25(3): 206-212), FPS1, FPS2, FPS3, or FPS-ZM1. In some embodiments, the anti-RAGE agent is FPS1, FPS2, or FPS3. In some embodiments, the anti-RAGE agent is not FPS-ZM1 or PF-04494700.

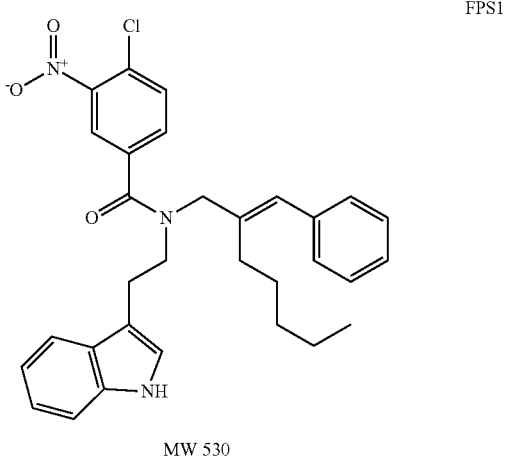

FPS1

MW 530

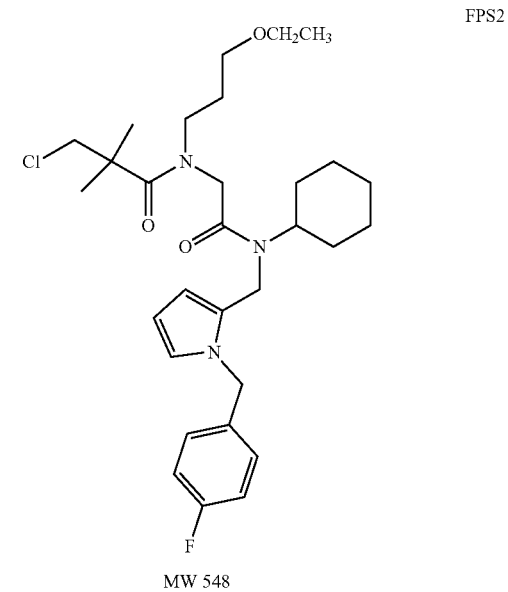

FPS2

MW 548

-continued

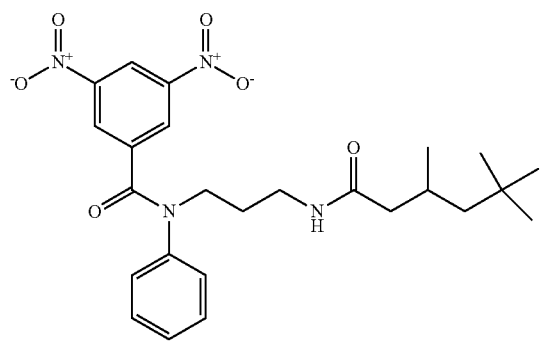

FPS3

MW 485

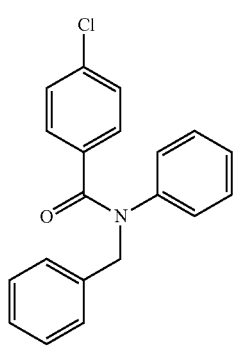

FPS-ZM1

MW 327

The term "antibody," as used herein, refers to an immunoglobulin molecule which specifically binds with an antigen. Methods of preparing antibodies are well known to those of ordinary skill in the science of immunology. Antibodies can be intact immunoglobulins derived from natural sources or from recombinant sources and can be immunoreactive portions of intact immunoglobulins. Antibodies are typically tetramers of immunoglobulin molecules. Tetramers may be naturally occurring or reconstructed from single chain antibodies or antibody fragments. Antibodies also include dimers that may be naturally occurring or constructed from single chain antibodies or antibody fragments. The antibodies in the present invention may exist in a variety of forms including, for example, polyclonal antibodies, monoclonal antibodies, Fv, Fab and F(ab') 2, as well as single chain antibodies (scFv), humanized antibodies, and human antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab') 2, and Fv fragments, linear antibodies, scFv antibodies, single-domain antibodies, such as camelid antibodies (Riechmann, 1999, Journal of Immunological Methods 231:25-38), composed of either a VL or a VH domain which exhibit sufficient affinity for the target, and multispecific antibodies formed from antibody fragments. The antibody fragment also includes a human antibody or a humanized antibody or a portion of a human antibody or a humanized antibody.

Antibodies can be made by any of the methods known in the art utilizing a polypeptide of the invention (e.g., RAGE polypeptide), or immunogenic fragments thereof, as an immunogen. One method of obtaining antibodies is to immunize suitable host animals with an immunogen and to follow standard procedures for polyclonal or monoclonal antibody production. The immunogen will facilitate presentation of the immunogen on the cell surface. Immunization of a suitable host can be carried out in a number of ways. Nucleic acid sequences encoding a polypeptide of the invention or immunogenic fragments thereof, can be provided to the host in a delivery vehicle that is taken up by immune cells of the host. The cells will in turn express the receptor on the cell surface generating an immunogenic response in the host. Alternatively, nucleic acid sequences encoding the polypeptide, or immunogenic fragments thereof, can be expressed in cells in vitro, followed by isolation of the polypeptide and administration of the polypeptide to a suitable host in which antibodies are raised.

Alternatively, antibodies against the polypeptide may, if desired, be derived from an antibody phage display library. A bacteriophage is capable of infecting and reproducing within bacteria, which can be engineered, when combined with human antibody genes, to display human antibody proteins. Phage display is the process by which the phage is made to 'display' the human antibody proteins on its surface. Genes from the human antibody gene libraries are inserted into a population of phage. Each phage carries the genes for a different antibody and thus displays a different antibody on its surface.

Antibodies made by any method known in the art can then be purified from the host. Antibody purification methods may include salt precipitation (for example, with ammonium sulfate), ion exchange chromatography (for example, on a cationic or anionic exchange column preferably run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

Antibodies can be conveniently produced from hybridoma cells engineered to express the antibody. Methods of making hybridomas are well known in the art. The hybridoma cells can be cultured in a suitable medium, and spent medium can be used as an antibody source.

Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition (e.g., Pristane).

By "biological sample" is meant any liquid, cell, or tissue obtained from a subject. In some embodiments, the biological sample is blood.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "pre-cachexia" is meant a clinical state that fails to meet the criteria for cachexia. For example, a subject may be pre-cachexic when their weight is stable or when their weight loss is about 1%, 2% or 3% of their body mass. As used with respect to the invention described herein, at least a subset of patients with pre-cachexia may be characterized by an increase in one or more S100 RAGE ligands and/or a decrease in soluble RAGE relative to a reference level without unintended weight loss of at least 5% or more of body weight.

By "cachexia" is meant unintended weight loss of at least 5% or more of body weight. In general, cachexia refers to the progressive loss of lean body mass (particularly of muscle mass) that typically is associated with gross body weight loss that is at least 5, 6, 7, 8, 9, 10% or more. Muscle and adipose tissue loss, indicative of cachexia, may be detected by a computed tomography (CT) scan (Martin et al., *J Clin Oncol* 31:1539-1547 (2013)), though this method has not been validated as sufficient to formally diagnose the condition as there are numerous conditions that result in similar findings by imaging studies alone. Currently, there is no molecular biomarker(s) for this condition, as the pathogenesis of cachexia remains to be elucidated. In some embodiments, cachexia is characterized by loss of myosin heavy chain.

By "cancer-induced cachexia" is meant cachexia associated with the presence of a cancer or tumor.

By "disease-induced cachexia" is meant cachexia associated with the presence of a disease that is not due to the presence of at least one cancer or tumor. As used herein, at least a subset of patients with disease-induced cachexia may be characterized by an increase in one or more S100 RAGE ligands and/or a decrease in soluble RAGE relative to a reference level.

By "cachexia-inhibitory activity" is meant an activity of an agent that inhibits cachectogenic signaling or cachexia in a cell or subject. In some embodiments, cachectogenic signaling or cachexia in a cell or subject is measured using the cachexia functional assay(s) described herein. In particular embodiments, cachexia-inhibitory activity of an agent is indicated by loss of myosin heavy chain in a cell. In certain embodiments, the agent is an antibody or a small molecular compound. Conversely, by "cachexia-inducing activity" is meant an activity of an agent that increases or promotes cachectogenic signaling or cachexia in a cell or subject. For example, the RAGE ligands S100 A7, S100A8, and S100A9, have cachexia-inducing activity.

By "cardiac dysfunction" or "heart dysfunction" is meant an alteration, particularly a decrease, in a heart function, structure, or activity. In some embodiments, the cardiac dysfunction is characterized by an irregular heartbeat. In certain embodiments, the cardiac dysfunction is cardiac atrophy. In some other embodiments, the cardiac dysfunction is characterized by loss of myosin heavy chain in a cardiomyocyte. In particular embodiments, the cardiac dysfunction is dependent on RAGE-mediated signaling. In some embodiments, the cardiac dysfunction follows an acute myocardial infarction. In still other embodiments, the cardiac dysfunction is cardiac ischemia.

In particular embodiments, the cardiac dysfunction is inhibited and/or prevented by an anti-RAGE antibody. In certain embodiments, the cardiac dysfunction is rescued or reversed by an anti-RAGE antibody.

The cardiac dysfunction can be dependent or independent of cachexia. By "cachexia-associated cardiac dysfunction" is meant a decrease or impairment in heart function or structure relative to normal heart function that is associated with the presence of cachexia. In some embodiments, the cardiac dysfunction is induced by cachexia. In some other embodiments, the cardiac dysfunction is associated with cancer-induced cachexia. In still other embodiments, cachexia is associated with advanced heart failure. In particular embodiments, the cachexia-associated cardiac dysfunction is cachexia-induced cardiac atrophy. In some embodiments, the cachexia-associated cardiac dysfunction is characterized by a loss of myosin heavy chain in a cardiomyocyte.

Currently, the pathogenesis of cachexia-associated cardiac dysfunction remains to be elucidated. However, without intending to be bound by theory, it is believed cachexia-associated cardiac dysfunction is depdendent on RAGE-mediated signaling. Thus, in some embodiments, a cachexia-associated cardiac dysfunction is inhibited, prevented, and/or reversed by inhibiting RAGE-mediated signaling. In some embodiments, the RAGE-mediated signaling is inhibited by contacting RAGE with an anti-RAGE antibody.

By "cardiomyocyte" is meant a cardiac muscle cell.

By "cardiac ischemia" is meant a lack of blood flow and/or oxygen to the heart muscles.

As used herein, "cellular differentiation" or "differentiation" is the process by which a less specialized cell becomes a more specialized cell type.

"Detect" refers to identifying the presence, absence or amount of the analyte to be detected.

By "disease" is meant any condition or disorder that damages or interferes with the normal function of a cell, tissue, or organ. In one embodiment, the disease is pre-cachexia, cachexia, or refractory cachexia. In another embodiment, the disease is cardiac dysfunction. In still another embodiment, the disease is cachexia-associated cardiac dysfunction. In another embodiment, the disease is cachexia-independent cardiac dysfunction.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The invention provides a number of targets that are useful for the development of highly specific drugs to treat or a disorder characterized by the methods delineated herein. In addition, the methods of the invention provide a facile means to identify therapies that are safe for use in subjects. In addition, the methods of the invention provide a route for analyzing virtually any number of compounds for effects on a disease described herein with high-volume throughput, high sensitivity, and low complexity.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

As used herein, a "functional site" on a RAGE polypeptide is a binding site on RAGE of an antibody or ligand having functional activity. In some embodiments, the functional activity is modulation of cachectic signaling or cachexia in a cell or subject. In some other embodiments, the functional activity is inhibition of cachectic signaling or cachexia in a cell or subject. In particular embodiments, the functional activity is measured using a cachexia functional assay described herein.

In some embodiments, the functional site of RAGE is on the V domain of RAGE. In some other embodiments, the functional site on RAGE comprises any one or more of amino acid residues 23-54 of RAGE. In still other embodiments, the functional site comprises any one or more amino acid residues 25, 54, 59, 61, 91, 92, 94, 96, 98, 114, 116, 150, 151, 152, 154, 175, 177, 178, 179, 186, 213, and 216 of RAGE.

By "heart failure" is meant a condition where the ability of the heart to pump blood is decreased. In particular embodiments, the ability of the heart to pump blood is decreased such that the heart is not able to pump blood sufficient to meet the body's needs.

"High-throughput screening" (HTS) refers to a process that uses a combination of modern robotics, data processing and control software, liquid handling devices, and/or sensitive detectors, to efficiently process a large amount of (e.g., thousands, hundreds of thousands, or millions of) samples in biochemical, genetic or pharmacological experiments, either in parallel or in sequence, within a reasonably short period of time (e.g., days). Preferably, the process is amenable to automation, such as robotic simultaneous handling of 96 samples, 384 samples, 1536 samples or more. A typical HTS robot tests up to 100,000 to a few hundred thousand compounds per day. The samples are often in small volumes, such as no more than 1 mL, 500 µl, 200 µl, 100 µl, 50 µl or less. Through this process, one can rapidly identify active compounds, small molecules, antibodies, proteins or polynucleotides which modulate a particular biomolecular/genetic pathway. The results of these experiments provide starting points for further drug design and for understanding the interaction or role of a particular biochemical process in biology. Thus "high-throughput screening" as used herein does not include handling large quantities of radioactive materials, slow and complicated operator-dependent screening steps, and/or prohibitively expensive reagent costs, etc.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any clinical indicator, protein, metabolite, or polynucleotide having an alteration associated with a disease or disorder. In one embodiment, an alteration in body mass, lean body mass, metabolism, or a metabolite is a marker (e.g., clinical indicator) of disease state (e.g., pre-cachexia or cachexia). In some embodiments, a marker of cachexia or cachexia-induced cardiac dysfunction is elevated level of a cachectogenic ligand (e.g., S100A7, S100A8, or S100A9).

By "metabolic profile" is meant alterations in one or more amino acid or lipid metabolites.

By "myocardial infarction" is meant a condition where blood flow to a part of the heart is stopped. Damage to heart muscle may result from a myocardial infarction.

As used herein, "obtaining" as in "obtaining an agent" includes synthesizing, purchasing, or otherwise acquiring the agent.

By "RAGE polypeptide" is meant a polypeptide or fragment thereof having at least about 85% or greater amino acid identity to the amino acid sequence provided at GenBank Accession No. AAH26069.1 and having RAGE biological activity. Exemplary RAGE biological activities include activity as a receptor for advanced glycation endproducts, binding to S100 proteins (e.g., S100A7, S100A8, S100A9), involvement in inflammatory and immune responses, and involvement in cachetogenic signaling. The exemplary RAGE polypeptide sequence at GenBank Accession No. AAH26069.1 is provided below:

```
  1 mdlwsagcvf yeiaslqplf pgvneldqis kihdvigtpa qkiltkfkqs ramnfdfpfk 61 kgsgiplltt nlspqclsll hamvaydpde riaahqalqh pyfqeqrkte kralgshrka
```

```
121 gfpehpvape plsnscqisk egrkqkqslk qeedrpkrrg payvmelpkl klsgvvrlss 181 yssptlqsvl gsgtngrvpv lrplkcipas kktdpqkdlk papqqcrlpt ivrkggr
```

By "RAGE polynucleotide" is meant a polynucleotide encoding a RAGE polypeptide. An exemplary RAGE polynucleotide sequence is provided at GenBank Accession No. AB036432.1. The exemplary sequence at GenBank Accession No. AB036432.1 is provided below.

sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

```
   1 gccaggaccc tggaaggaag caggatggca gccggaacag cagttggagc ctgggtgctg 61 gtcctcagtc tgtgggggc  agtagtaggt gctcaaaaca tcacagcccg gattggcgag 121 ccactggtgc tgaagtgtaa gggggcccc  aagaaaccac cccagcggct ggaatggaaa 181 ctgaacacag gccggacaga agcttggaag gtcctgtctc cccagggagg aggccctgg 241 gacagtgtgg ctcgtgtcct tcccaacggc tccctcttcc ttccggctgt cgggatccag 301 gatgagggga ttttccggtg ccaggcaatg aacaggaatg gaaaggagac caagtccaac 361 taccgagtcc gtgtctacca gattcctggg aagccagaaa ttgtagattc tgcctctgaa 421 ctcacggctg gtgttcccaa taaggtgggg acatgtgtgt cagagggaag ctaccctgca 481 gggactctta gctggcactt ggatgggaag ccctggtgc  ctaatgagaa gggagtatct 541 gtgaaggaac agaccaggag acaccctgag acagggctct tcacactgca gtcggagcta 601 atggtgaccc cagcccgggg aggagatccc cgtcccacct tctcctgtag cttcagccca 661 ggccttcccc gacaccgggc cttgcgcaca gccccatcc  agcccgtgt  ctgggagcct 721 gtgcctctgg aggaggtcca attggtggtg gagccagaag gtggagcagt agctcctggt 781 ggaaccgtaa ccctgacctg tgaagtccct gcccagccct ctcctcaaat ccactggatg 841 aaggatggtg tgcccttgcc ccttcccccc agccctgtgc tgatcctccc tgagataggg 901 cctcaggacc agggaaccta cagctgtgtg gccacccatt ccagccacgg gccccaggaa 961 agccgtgctg tcagcatcag catcatcgaa ccaggcgagg aggggccaac tgcaggctct 1021 gtgggaggat cagggctggg aactctagcc ctggccctgg ggatcctggg aggcctgggg 1081 acagccgccc tgctcattgg ggtcatcttg tggcaaaggc ggcaacgccg aggagaggag 1141 aggaaggccc cagaaaacca ggaggaagag gaggagcgtg cagaactgaa tcagtcggag 1201 gaacctgagg caggcgagag tagtactgga gggccttgag gggcccacag acagatccca 1261 tccatcag
```

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid By "S100A7 polypeptide" is meant a polypeptide or fragment thereof having at least about 85% or greater amino acid identity to the amino acid sequence provided at NCBI Accession No. NP_002954.2 and having the activities of binding to a RAGE polypeptide and inhibiting cachexia. The exemplary S100A7 polypeptide sequence at NCBI Accession No. NP_002954.2 is provided below:

```
  1 msntqaersi igmidmfhky trrddkiekp slltmmkenf pnflsacdkk gtnyladvfe 61 kkdknedkki dfseflsllg diatdyhkqs hgaapcsggs q
```

By "S100A7 polynucleotide" is meant a polynucleotide encoding a S100A7 polypeptide. An exemplary S100A7 polynucleotide sequence is provided at NCBI Accession No. NM_002963.3. The exemplary sequence at NCBI Accession No. NM_002963.3 is provided below.

```
  1 gtccaaacac acacatctca ctcatccttc tactcgtgac gcttcccagc tctggctttt 61 tgaaagcaaa gatgagcaac actcaagctg agaggtccat aataggcatg atcgacatgt 121 ttcacaaata caccagacgt gatgacaaga ttgagaagcc aagcctgctg acgatgatga 181 aggagaactt ccccaacttc cttagtgcct gtgacaaaaa gggcacaaat tacctcgccg 241 atgtctttga gaaaaaggac aagaatgagg ataagaagat tgatttttct gagtttctgt 301 ccttgctggg agacatagcc acagactacc acaagcagag ccatggagca gcgccctgtt 361 ccggggggcag ccagtgaccc agccccacca atgggcctcc agagacccca ggaacaataa 421 aatgtcttct cccaccagaa aaaaaaaaa
```

By "S100A8 polypeptide" is meant a polypeptide or fragment thereof having at least about 85% or greater amino acid identity to the amino acid sequence provided at NCBI Accession No. NP_002955.2 and having the activities of binding to a RAGE polypeptide and inhibiting cachexia. The exemplary S100A8 polypeptide sequence at NCBI Accession No. NP_002955.2 is provided below:

```
 1  mltelekaln siidvyhkys likgnfhavy rddlkkllet ecpqyirkkg advwfkeldi 61  ntdgavnfqe flilvikmgv aahkkshees hke
```

By "S100A8 polynucleotide" is meant a polynucleotide encoding a S100A8 polypeptide. An exemplary S100A8 polynucleotide sequence is provided at NCBI Accession No. NM_002964.4. The exemplary sequence at NCBI Accession No. NM_002964.4 is provided below.

```
  1 gagaaaccag agactgtagc aactctggca gggagaagct gtctctgatg gcctgaagct 61 gtgggcagct ggccaagcct aaccgctata aaaaggagct gcctctcagc cctgcatgtc 121 tcttgtcagc tgtctttcag aagacctggt ggggcaagtc cgtgggcatc atgttgaccg 181 agctggagaa agccttgaac tctatcatcg acgtctacca caagtactcc ctgataaagg 241 ggaatttcca tgccgtctac agggatgacc tgaagaaatt gctagagacc gagtgtcctc 301 agtatatcag gaaaaagggt gcagacgtct ggttcaaaga gttggatatc aacactgatg 361 gtgcagttaa cttccaggag ttcctcattc tggtgataaa gatgggcgtg gcagcccaca 421 aaaaaagcca tgaagaaagc cacaaagagt agctgagtta ctgggcccag aggctgggcc 481 cctggacatg tacctgcaga ataataaagt catcaatacc tcaaaaaaaa aa
```

By "S100A9 polypeptide" is meant a polypeptide or fragment thereof having at least about 85% or greater amino acid identity to the amino acid sequence provided at NCBI Accession No. NP_002956.1 and having the activities of binding to a RAGE polypeptide and inhibiting cachexia. The exemplary S100A9 polypeptide sequence at NCBI Accession No. NP_002956.1 is provided below:

```
 1 mtckmsqler nietiintfh qysvklghpd tlnqgefkel vrkdlqnflk kenknekvie 61 himedldtna dkqlsfeefi mlmarltwas hekmhegdeg pghhhkpglg egtp
```

By "S100A9 polynucleotide" is meant a polynucleotide encoding a S100A9 polypeptide. An exemplary S100A9 polynucleotide sequence is provided at NCBI Accession No. NM_002965.3. The exemplary sequence at NCBI Accession No. NM_002965.3 is provided below.

```
  1 aaacactctg tgtggctcct cggctttgac agagtgcaag acgatgactt gcaaaatgtc 61 gcagctggaa cgcaacatag agaccatcat caacaccttc caccaatact ctgtgaagct 121 ggggcaccca gacaccctga accaggggga attcaaagag ctggtgcgaa aagatctgca 181 aaattttctc aagaaggaga ataagaatga aaaggtcata gaacacatca tggaggacct 241 ggacacaaat gcagacaagc agctgagctt cgaggagttc atcatgctga tggcgaggct 301 aacctgggcc tcccacgaga agatgcacga gggtgacgag ggccctggcc accaccataa 361 gccaggcctc ggggagggca cccctaaga ccacagtggc caagatcaca gtggccacgg 421 ccacggccac agtcatggtg gccacggcca cagccactaa tcaggaggcc aggccaccct 481 gcctctaccc aaccagggcc ccgggggcctg ttatgtcaaa ctgtcttggc tgtggggcta 541 ggggctgggg ccaaataaag tctcttcctc caagtcaaaa aaaaaa
```

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 .mu.g/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline. In one aspect, the subject is a human.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 13 is a schematic depicting generation and characterization of a cardiac cachexia model using cardiomyocytes differentiated from induced pluripotent stem cells (iPS cells).

FIG. 14 shows a loss of myosin heavy chain in cardiomyocytes treated with a cachexia-inducing medium described herein (right) relative to cardiomyocytes not treated with cachexia-inducing medium (left). Light gray indicates myosin heavy chain (MYHC).

FIG. 16 is a set of micrographs showing cardiac atrophy and cardiac dysfunction is reversed by an anti-RAGE antibody. The micrographs on the left show DAPI stained and myosin heavy chain (MYHC) stained cardiomyocytes. On the left, the top micrograph shows loss of myosin heavy chain in cardiomyocytes treated with cachexia inducing medium. The bottom micrograph on the left shows myosin heavy chain restored in those cardiomyocytes after treatment with an anti-RAGE antibody. The micrograph on the right is from a videomicrograph showing that regular heart beat was restored in cardiac tissue in cachexia-inducing medium following treatment of the cardiac tissue with anti-RAGE antibody.

FIG. 19 is a table showing anti-RAGE antibodies screened in a cachexia functional assay described herein.

FIG. 22 is a table showing anti-RAGE antibodies screened in a cachexia functional assay described herein. Out of the 22 candidate antibodies screened, two (2) antibodies, antibody D and antibody X, were identified as having cachexia-inhibitory activity.

Figure 1:
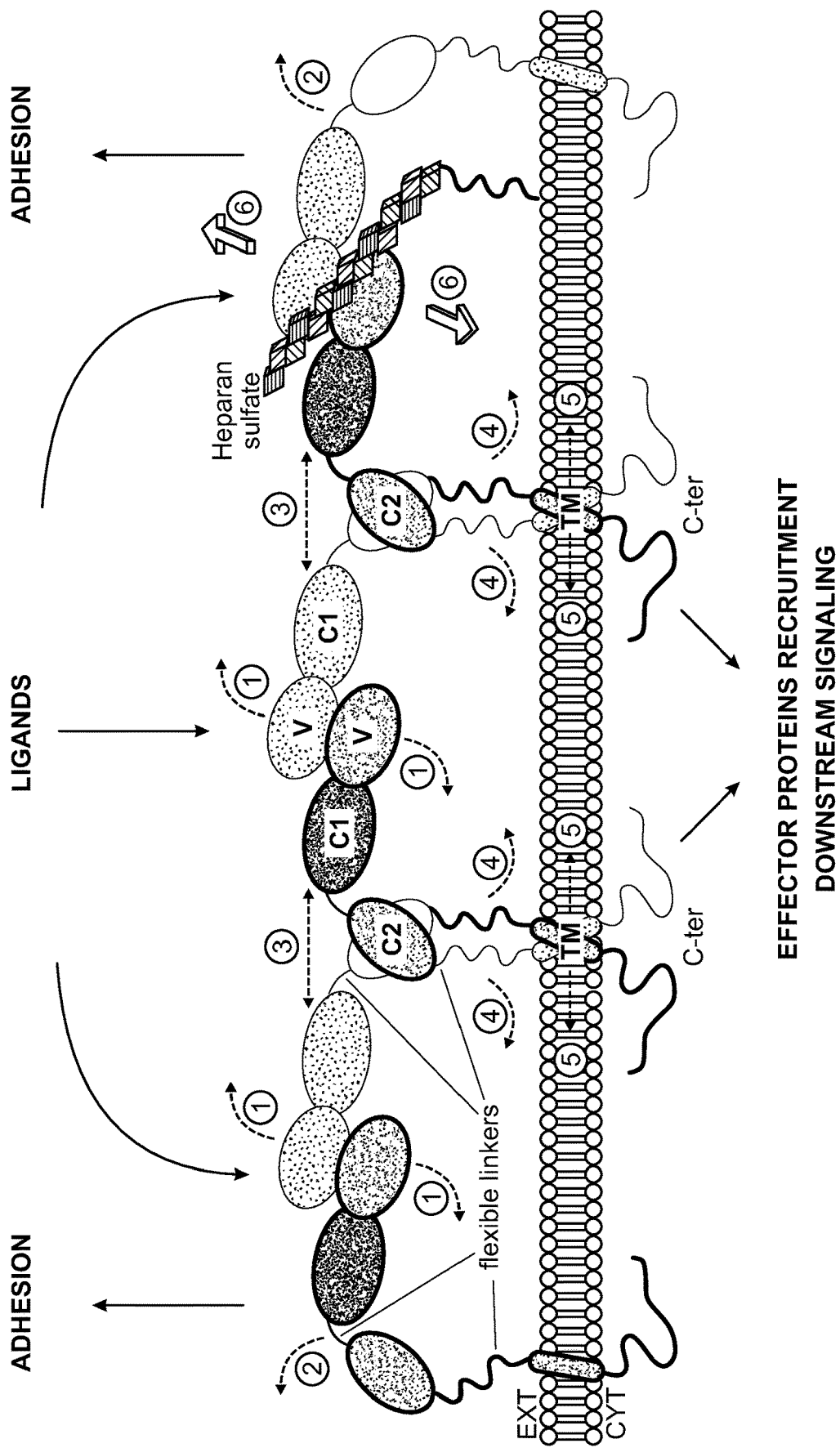
FIG. 1 is a schematic illustrating a current model of RAGE oligomerization (Yatime and Andersen, FEBS Journal 280 (2013) 6556-6568).

Appendix A (beginning at page 50) provides a PDB file listing atomic coordinates of a domain of RAGE. The PDB file is available at Protein Data Bank PDB ID 4LP4.

DETAILED DESCRIPTION OF THE INVENTION

The invention provides compositions and methods for treating a cardiac dysfunction, as well as methods for the discovery or identification of therapeutic agents useful for inhibiting cachexia.

The invention is based, at least in part, on the discovery that anti-RAGE antibodies prevented and/or reversed cardiac dysfunction and cardiac atrophy in cardiomyocytes. Accordingly, the invention provides methods of treating cardiac dysfunction in a subject using anti-RAGE antibodies. The invention is further based, at least in part, on the discovery of functional sites on the RAGE polypeptide and cachectogenic ligands of RAGE. In some embodiments, the functional site is a binding site of a cachexia-inhibitory anti-RAGE antibody. In some other embodiments, the functional site is a binding site of a cachexia-inducing ligand. Without intending to be bound by theory, binding of agents to the functional sites is believed to disrupt RAGE-mediated cachectogenic signaling in cells by disrupting oligomerization and/or formation of a "raft" of RAGE and/or RAGE ligands on a cell surface.

In Vitro Cachexia/Pre-Cachexia Model System

The present invention provides a culture system, comprising a human target cell and a cachexia-inducing factor. In certain embodiments, the target cell is selected from a myocyte, an adipocyte, and a hepatocyte. In one embodiment, the target cell is a cardiomyocyte.

In certain embodiments, the cachexia-inducing factor is provided in (i) human plasma from a cachexia patient or (ii) cachexia-inducing conditioned media, such as human cancer cell conditioned media. In certain embodiments, the media is conditioned by a human cancer cell line selected from one or more of the following: AsPC-1, A375, CAPAN-1, CAPAN-2, C32, G361, HCT-15, HPAF-II, JHU012, JHU022, LS180, LX1, MKN1, and PANC-1. In particular embodiments, a cachexia-inducing cell line is the human melanoma cell line A375 (ATCC® CRL1619™); the intestinal human colon adenocarcinoma cell line LS180 (ATCC® CL-187™); the hepatic stellate cell line LX1 (Xu et al., Gut. January 2005; 54(1): 142-151); the malignant melanoma human cell line G361 (ATCC® CRL-1424™), or the human malignant melanoma cell line C32 (ATCC® CRL-1585™). In certain embodiments, the media is conditioned by a human cancer cell isolated from a patient.

In certain embodiments, the culture is in a single or a multi-well plate format. In certain embodiments, the invention provides a multi-well plate suitable for use in a high-throughput screening system, the plate having a plurality of wells comprising the culture system described therein. The surface of the multi-well plate may be the surface of a culture well or glass slide, or any other suitable surface. In certain embodiments the multi-well plate contains 384 wells. Cultures can be contained in a multi-well plate having a 96-, 384-, 1536- or more than 1536-well format.

In certain embodiments, the invention further provides a method for producing the model of the present invention, in a single or multi-well plate format.

Uses of the Cachexia/Pre-cachexia Model System

The present invention provides methods for characterizing an agent for the ability to induce pre-cachexia or cachexia in a target cell. The method generally involves contacting or exposing a target cell to a test agent, and characterizing the effect of the agent on the target cell relative to: (i) a control target cell not exposed to the test agent; or (ii) a transcriptional profile of a non-cachectic cell and/or a transcriptional profile of a cachectic cell, wherein the cell type of the target cell and the cachectic and/or non-cachectic cell is the same.

The present invention provides a method for predicting the effect of a test agent on a target cell of a patient in vivo, comprising culturing a target cell obtained from a patient in the system of the invention, exposing it to the test agent, and assaying for a pharmacological effect of the test agent on the target cell relative to: (i) a control target cell not treated with the test agent; or (ii) a transcriptional profile of a non-cachectic cell and/or a transcriptional profile of a cachectic cell, wherein the cell type of the target cell and the cachectic and/or non-cachectic cell is the same.

In certain embodiments, the target cell is isolated from a patient with cancer or a cardiac disease.

In certain embodiments, the effect is selected from proliferation, viability, and differentiation, or combinations thereof.

In certain embodiments, the effect is detected by assessing a change in gene expression profile between the target cell and the control target cell of step (i); or the cachectic or non-cachectic cell of step (ii).

In certain embodiments, the target cell is selected from a myocyte, an adipocyte, and a hepatocyte. In a particular embodiment, the target cell is a cardiomyocyte.

The cachectic culture system can be used to screen for test agents (such as solvents, small molecule drugs, peptides, and polynucleotides) or environmental conditions (such as culture conditions or manipulation) that affect the characteristics of cells. Two or more agents can be tested in combination (by exposing to the cells either simultaneously or sequentially), to detect possible drug-drug interactions and/or rescue effects (e.g., by testing a toxin and a potential anti-toxin). Agent(s) and environmental condition(s) can be tested in combination (by treating the cells with a drug either simultaneously or sequentially relative to an environmental condition), to detect possible agent-environment interaction effects.

In certain embodiments, the assay to determine the characteristics of cells is selected in a manner appropriate to the cell type and agent and/or environmental factor being studied as disclosed in WO 2002/04113, which is hereby incorporated by reference in its entirety. For example, changes in cell morphology may be assayed by standard light, or electron microscopy. Alternatively, the effects of treatments or compounds potentially affecting the expression of cell surface proteins may be assayed by exposing the cells to either fluorescently labeled ligands of the proteins or antibodies to the proteins and then measuring the fluorescent emissions associated with each cell on the plate. As another example, the effects of treatments or compounds which potentially alter the pH or levels of various ions within cells may be assayed using various dyes which change in color at determined pH values or in the presence of particular ions. The use of such dyes is well known in the art. For cells which have been transformed or transfected with a genetic marker, such as the β-galactosidase, alkaline phosphatase, or luciferase genes, the effects of treatments or compounds may be assessed by assays for expression of that marker. In particular, the marker may be chosen so as to cause spectrophotometrically assayable changes associated with its expression.

Particular screening applications of this invention relate to the testing of pharmaceutical compounds in drug research. The reader is referred generally to the standard textbook *In vitro Methods in Pharmaceutical Research*, Academic Press, 1997, and U.S. Pat. No. 5,030,015. In certain aspects of this invention, the culture of the invention is used to grow and differentiate a cachectic target cell to play the role of test cells for standard drug screening and toxicity assays. Assessment of the activity of candidate pharmaceutical compounds generally involves combining the target cell (e.g., a cardiomyocyte, an adipocyte or a hepatocyte) with the candidate compound, determining any change in the morphology, marker phenotype, or metabolic activity of the cells that is attributable to the candidate compound (compared with untreated cells or cells treated with an inert compound, such as vehicle), and then correlating the effect of the candidate compound with the observed change. The screening may be done because the candidate compound is designed to have a pharmacological effect on the target cell, or because a candidate compound may have unintended side effects on the target cell. Alternatively, libraries can be screened without any predetermined expectations in hopes of identifying compounds with desired effects.

Cytotoxicity can be determined in the first instance by the effect on cell viability and morphology. In certain embodiments, toxicity may be assessed by observation of vital staining techniques, ELISA assays, immunohistochemistry, and the like or by analyzing the cellular content of the culture, e.g., by total cell counts, and differential cell counts or by metabolic markers such as MTT and XTT.

Additional further uses of the culture of the invention include, but are not limited to, its use in research e.g., to elucidate cachectic mechanisms leading to the identification of novel targets for cachectic therapies, and to generate genotype-specific cells for disease modeling, including the generation of new therapies customized to different genotypes. Such customization can reduce adverse drug effects and help identify therapies appropriate to the patient's genotype.

Methods of Identifying a Subject Having Cachexia or Cachexia-Associated Disease

As reported herein below, within days of contacting target cells with cachexia-inducing media changes in metabolism, metabolite profiles, the differential expression of markers, and changes in cell morphology are observed. Such changes closely phenocopy overt clinical cachexia as induced by cachectic patient plasma and seen in patient biopsy samples, and likely reproduce the alterations present in pre-cachectic humans and mice. Significantly, many of the changes observed in cells in vitro in response to cachexia inducing factors were reversible (e.g., the cachectic gene expression signature, loss of myosin heavy chain, loss of lipid content, and cell atrophy) with novel treatments identified with this discovery platform The presence and/or level of the cachexia-inducing proteins, e.g. the factors listed in Table 2, in patient plasma may serve as cachectic biomarker(s) useful for diagnosing and/or monitoring a patient with cachexia. Accordingly, the present invention also provides a method for diagnosing a patient with cachexia, comprising (i) obtaining plasma from the patient; and (ii) detecting the presence or level of a cachexia-inducing factor(s) selected from Table 2. The present invention also provides a method for monitoring a patient with cachexia, comprising (i) obtaining plasma from the patient; and (ii) detecting the presence or level of a cachexia-inducing factor(s) selected from Table 2.

TABLE 2

| Cachexia-Inducing Factors | |
|---|---|
| BCAM | NGF |
| BTC | PDGFA |
| CCL5 | PDGFB |
| CCL28 | Plasminogen activator inhibitor 1 |
| DKK3 | S100A7 |
| EGFR | S100A8 |
| Follistatin-related peptide 1 | S100A9 |
| HMG1 | S100A11 |
| IGF-2 | sRAGE (soluble RAGE)* |
| IGFBP-2 | TNFRSF10C |
| IGFBP-6 | TNFSF18 |
| IL6 | TYRO3 |
| Lipolysis-stimulated lipoprotein receptor | |
| BCAM | |
| BTC | |

(*anti-correlated with cachexia)

In particular embodiments, at least one or more of IGFBP-1, CCL27, AXL, CSF1, ICAM2, PlGF, TMP2, FGF4, KDR and CSF3 are increased in cachexia.

In other embodiments, a marker of cachexia or pre-cachexia or a cachexia-associated disease (e.g., cachexia-associated cardiac dysfunction) is any one or more of three markers selected from S100A2 or S100A4, S100A8 or S100A9, and S100A7; four markers selected from S100A2 or S100A4, S100A8 or S100A9, S100A7 and S100A14; five markers selected from S100A2 or S100A4, S100A8 or S100A9, S100A7, S100A14, and S100P, which are increased in pre-cachexia or cachexia. In particular embodiments, a marker of cachexia is S100A7, S100A8, or S100A9. In certain embodiments, a marker of cachexia-associated cardiac dysfunction is S100A7, S100A8, or S100A9.

In other embodiments, a marker of cachexia or pre-cachexia is Basal cell adhesion molecule (BCAM), Buch-ang-tang (BCT), Chemokine ligand (CCL)5, CCL28, Dickkopf-related protein 3 (DKK3), Epidermal Growth Factor Receptor (EGFR), FASLG (Fas ligand), Fibroblast growth factor 4 (FGF4), Follistatin-related peptide 1, intercellular adhesion molecule (ICAM2), High Mobility Group (HMG1), Insulin Growth Factor-2 (IGF-2), Insulin Growth Factor Binding Protein-2 (IGFBP-2), IGFBP-6, interleukin-6 (IL6), Kinase insert domain receptor (KDR), lipolysis-stimulated receptor (LSR), NM (NME/NM23 Nucleoside Diphosphate Kinase 1), Nerve Growth Factor (NGF), Platelet Derived Growth Factor-A (PDGFA), PDGFB, P1GF (placenta growth factor), tyrosine-protein kinase receptor (TYRO3), Plasminogen activator inhibitor 1, tissue inhibitor of metalloproteinases (TIMP2), soluble Receptor for Advanced Glycation Endproducts (sRAGE)*, Tumor necrosis factor receptor superfamily member 10C (TNFRSF10C), and tumor necrosis factor superfamily member 18 (TNFSF18). All of the aforementioned markers are increased, with the exception of sRAGE, which is decreased. In other embodiments, the method further involves measuring an increase in an S100 family member selected from HMGB1, S100P, S100A2, S100A3, S100A4, S100A5, S100A7, S100A7A, S100A8, S100A9, S100A11, S100A12, S100A13, S100A14, and S100A15.

In some embodiments, the patient has a disease-related cachexia that is not associated with cancer, but that like cancer-induced cachexia fails to respond to treatment with nutritional support and anti-inflammatory therapy. Such disease-related cachexia may, for example, be associated with AIDS, chronic obstructive lung disease, or cardiac dysfunction (e.g., congestive heart failure) and, like cancer-induced cachexia are characterized by an increase in one or more S100 RAGE ligands and/or a decrease in soluble RAGE relative to a reference level.

In certain embodiments, the target cell is selected from a myocyte, an adipocyte, and a hepatocyte. In a particular embodiment, the target cell is a cardiomyocyte.

The presence or absence of the herein disclosed marker(s) is measured in a tissue (e.g., biopsy) or bodily fluid from a pre-cachectic or cachectic subject. Bodily fluids used to evaluate the presence or absence of the herein disclosed markers include without limitation blood, serum, plasma, urine, and or saliva. For example, levels of biomarker are measured in the blood or biopsy before and after treatment in a subject.

Biopsy refers to the removal of a sample of tissue for purposes of diagnosis. For example, a biopsy is from a muscle, fat, a cancer or tumor, including a sample of tissue from an abnormal area or an entire tumor.

Also provided is a method of predicting or monitoring the efficacy of an anti-cachectic agent (e.g., an anti-RAGE antibody) in a subject. The method comprises acquiring a biological sample, such as tissue or bodily fluid, from the subject after administering the agent to the subject. For example, the tissue or bodily fluid is collected from the subject 1 to 60 minutes, hours, days, or weeks after administering the agent to the subject. The method further comprises detecting levels of one or more biomarkers delineated herein (e.g., S100 family proteins). A decrease in level(s) of one or more biomarkers is evidence of treatment efficacy. Thus, a decline in said increase or time is evidence of decreasing efficacy. Thus, it is preferred that biological samples be systematically acquired over time to monitor changes in marker levels.

Methods of Treatment

The present invention provides methods of treating cardiac dysfunction, particularly cachexia-associated and/or RAGE-associated cardiac dysfunction, and/or disorders or symptoms thereof which comprise administering a therapeutically effective amount of a pharmaceutical composition comprising an anti-RAGE agent as described herein, to a subject (e.g., a mammal such as a human). Thus, one embodiment is a method of treating a subject suffering from or susceptible to a cardiac disease or disorder or symptom thereof. The method includes the step of administering to the mammal a therapeutic amount of an amount of an anti-RAGE agent (e.g., anti-RAGE antibody) sufficient to treat the disease or disorder or symptom thereof, under conditions such that the disease or disorder is treated. Such treatment will be suitably administered to subjects, particularly humans, suffering from, having, susceptible to, or at risk for cardiac dysfunction (particularly cachexia-associated and/or RAGE-associated cardiac dysfunction), disorder, or symptom thereof. Determination of those subjects "at risk" can be made by any objective or subjective determination by a diagnostic test or opinion of a subject or health care provider (e.g., genetic test, enzyme or protein marker (such as levels of S100 ligands), family history, and the like). The compounds herein may be also used in the treatment of any other disorders in which RAGE-mediated signaling may be implicated.

The methods herein include administering to the subject (including a subject identified as in need of such treatment) an effective amount of an anti-RAGE antibody an agent inhibiting RAGE-mediated signaling as described herein, or a composition described herein to produce such effect. Identifying a subject in need of such treatment can be in the judgment of a subject or a health care professional and can be subjective (e.g. opinion) or objective (e.g. measurable by a test or diagnostic method).

In one aspect, the present invention provides a method of treating, reversing, and/or preventing cardiac dysfunction, particularly cachexia-associated and/or RAGE-associated cardiac dysfunction, in a patient, comprising administering to a patient in need thereof an effective dose of anti-RAGE antibody, or an antigen-binding fragment thereof. The anti-RAGE antibody inhibits the RAGE signaling pathway. As described herein, without being bound by theory, activation of RAGE was associated with the cachectic phenotype and cachexia-induced cardiac atrophy and/or dysfunction.

In another aspect, the present invention provides a method of treating, reversing, and/or preventing cardiac dysfunction, particularly cachexia-associated and/or RAGE associated cardiac dysfunction, in a patient, comprising administering to a patient in need thereof an effective dose of a compound that inhibits the RAGE signaling pathway, or a pharmaceutically acceptable salt or prodrug thereof. In some embodiments, the compound is FPS3.

Figure 3A:
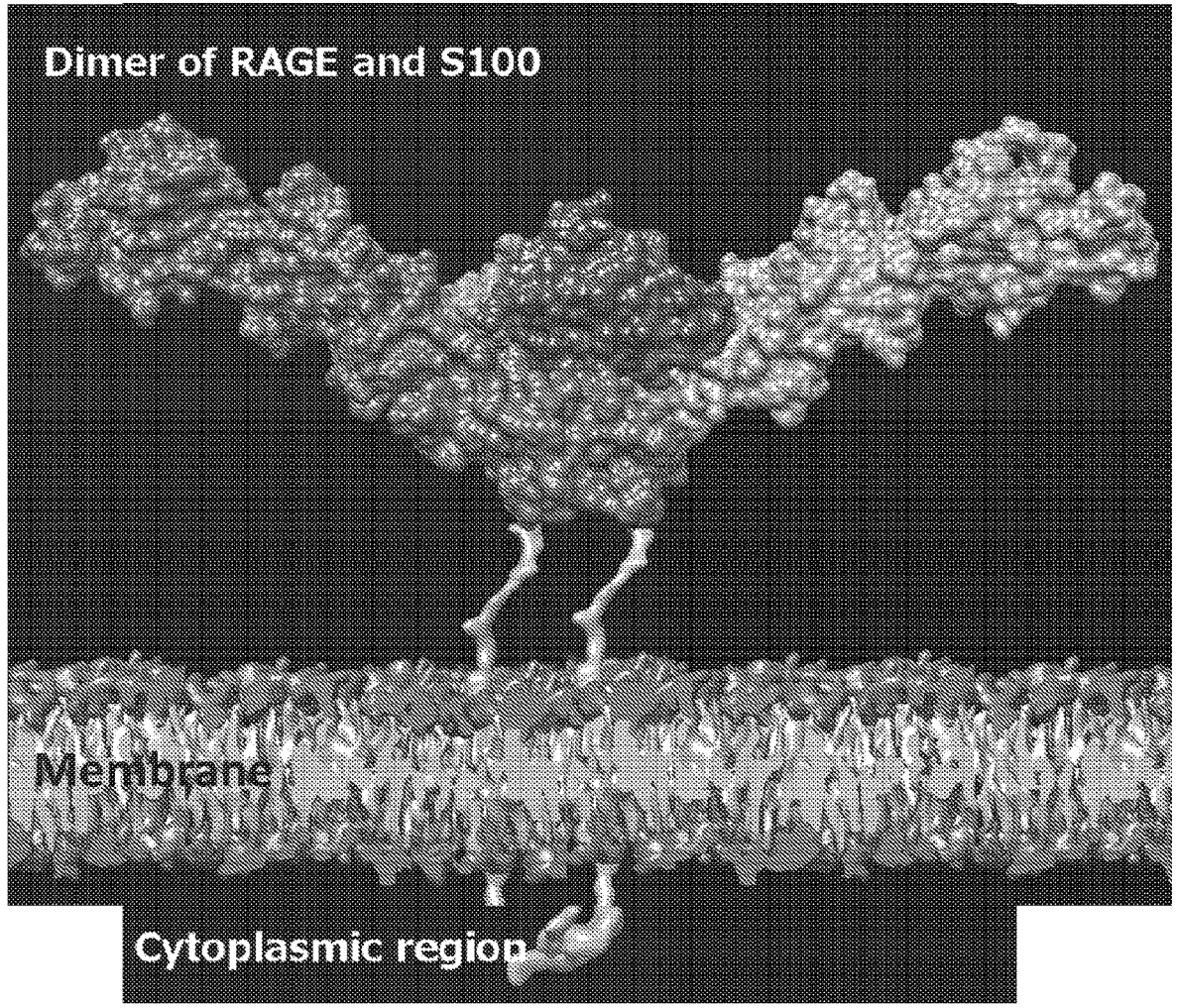
FIG. 3A is a schematic illustrating a dimer of RAGE and S100 (a ligand of RAGE).
Figure 3B:
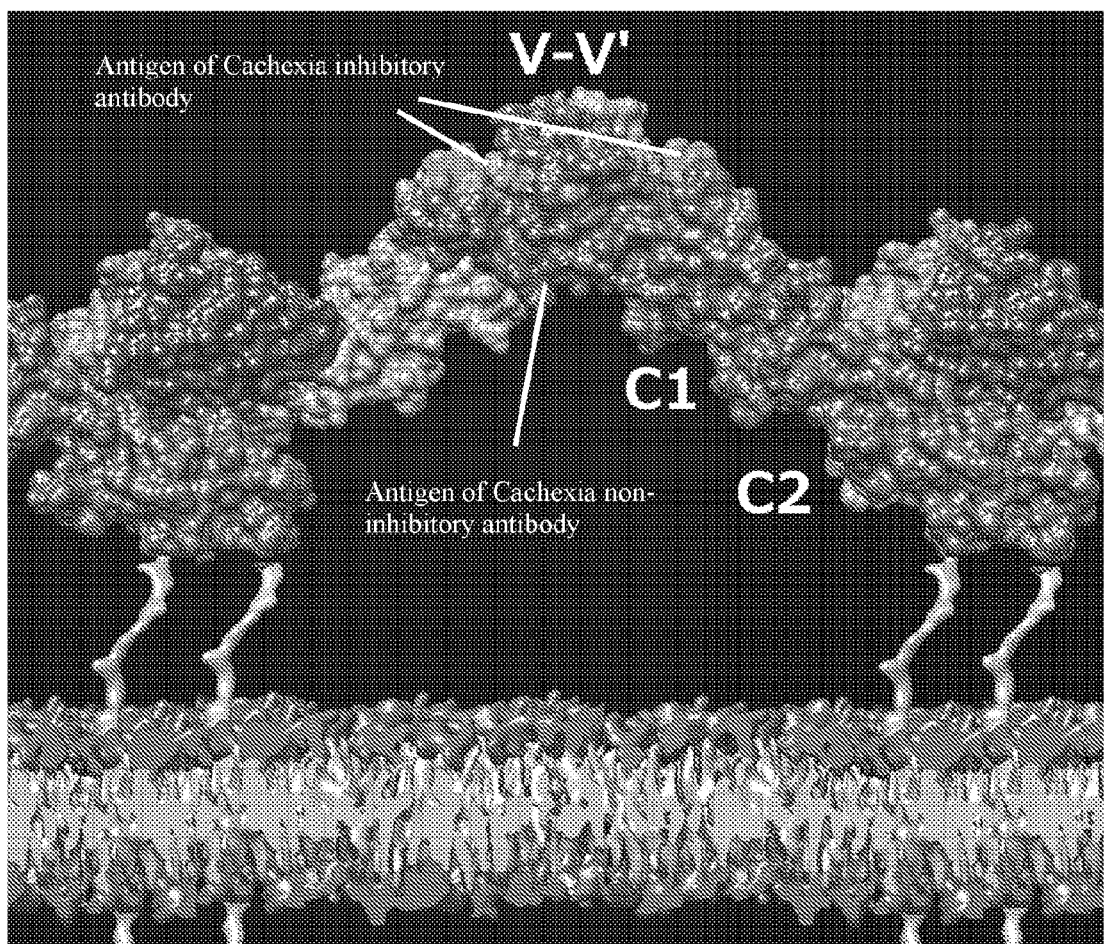
FIG. 3B is a schematic showing the antigen of a cachexia inhibitory antibody (residues 23-54) and the antigen of a cachexia non-inhibitory antibody (residues 23-43), each located on the V domain of RAGE. The structure of the V-V dimer is provided at PDB ID: 4LP4 and the structure of the RAGE+S100A6 dimer is at PDB ID: 4P2Y.
Figure 6A:
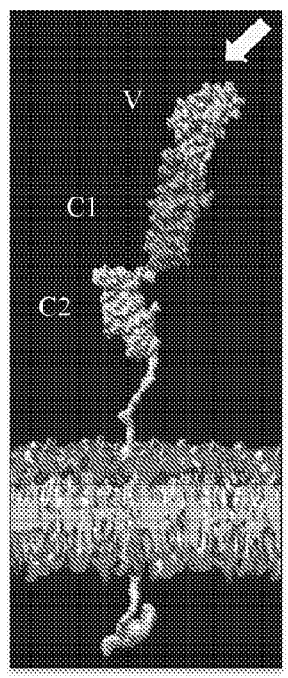
FIG. 6A is a schematic showing the structure of a RAGE polypeptide. The RAGE polypeptide is a transmembrane protein, having an intracellular, cytoplasmic tail; a transmembrane domain; and an extracellular domain comprised of the domains C2, C1, and V. The V domain of RAGE contains druggable "hot spots." The "hot spot" is a site on RAGE which, when bound by an agent (e.g., an antibody or small molecule), produce a functional effect such as inhibition of cachectic signaling or a cachectic phenotype. Thus, these functional sites on RAGE may serve as targets for rational drug design.

In certain embodiments, the compound or antibody inhibits a biological function or activity of the Receptor for Advanced Glycation Endproducts (RAGE). RAGE is a member of the immunoglobulin supergene family of molecules and was identified herein to be transcriptionally upregulated in muscle cells exposed to a cachexia-inducing factor(s). The extracellular (N-terminal) domain of RAGE includes three immunoglobulin-type regions: one V (variable) type domain followed by two C-type (constant) domains (see, e.g., FIG. 1; FIGS. 3A-3B; FIG. 6A) (Neeper et al., J Biol Chem 267:14998-15004 (1992); and Schmidt et al., Circ (Suppl) 96#194 (1997)). A single transmembrane-spanning domain and a short, highly charged cytosolic tail follow the extracellular domain. The N-terminal, extracellular domain can be isolated by proteolysis of RAGE or by molecular biological approaches to generate soluble RAGE (sRAGE) comprising the V and C domains. RAGE is believed to dimerize via interactions between the V domains. FIG. 1 illustrates a current model of RAGE oligomerization (Yatime and Andersen, FEBS Journal 280 (2013) 6556-6568).

Soluble RAGE (a negative regulator of RAGE signaling that acts as a sink for RAGE ligands) was also identified herein to be elevated in non-cachexia-inducing conditioned media in comparison to cachexia-inducing conditioned media. Additionally, treatment with a blocking peptide or antibody to RAGE has been shown to inhibit and reverse the cachexia-induced loss of myosin heavy chain protein in human muscle cells in vitro. RAGE blocking peptides are known in the art (see, for example, Arumugam et al., Clin Cancer Res. 2012; 18(16): 10.1158/1078-0432.CCR-12-0221), and are commercially available (e.g., RAP; a 10 amino acid sequence from S100P (R&D Systems)).

RAGE binds to multiple functionally and structurally diverse ligands, such as proteins having β-sheet fibrils characteristic of amyloid deposits and pro-inflammatory mediators, and includes amyloid beta (Aβ), serum amyloid A (SAA), Advanced Glycation End products (AGEs), S100 (a proinflammatory member of the Calgranulin 65 family), carboxymethyl lysine (CML), Mac-1, β32-integrin, CD11b/CD18 and high-mobility group protein 1 (HMG1), which is also known as high-mobility group protein box-1 (HMGB1) or amphoterin (Bucciarelli et al., Cell Mol Life Sci 59:1117-1128 (2002); Chavakis et al., Microbes Infect 6:1219-1225 (2004); Kokkola et al., Scand J Immunol 61:1-9 (2005); Schmidt et al., J Clin Invest 108:949-955 (2001); Rocken et al., Am J Pathol 162:1213-1220 (2003); Donato et al., Curr Mol Med 13(1): 24-57 (2013)).

The invention also provides methods for inhibiting RAGE by alternative means, such as with the use of small organic molecules, soluble receptor fragments, fusion proteins, antibodies or peptides, as disclosed in WO2011/042548, WO2007/109747, WO2009/136382, WO2011053707, WO2007/109749, WO2008/137552, WO2004/016229, US2010/0226915A1 and U.S. Pat. Nos. 7,981,424, 7,485,697 and 8,420,083, which are hereby incorporated by reference for the compounds and methods for inhibiting RAGE disclosed therein.

In one embodiment, the soluble receptor is a human soluble RAGE polypeptide (bold) fused to a mouse IgG2A Fc chimera (underline):

MAAGTAVGAWVLVLSLWGAVVGAQNITARIGE-PLVLKCKGAPKKPPQRLEWKLNT GRTEAWKVL-SPQGGGPWDSVARVLPNGSLFLPAVGIQDEGI-FRCQAMNRNGKETK SNYRVRVYQIPGKPEIVDSASELT-AGVPNKVGTCVSEGSYPAGTLSWHLDGKPLV PNEKGVSVKEQTRRHPETGLFTLQSELMVT-PARGGDPRPTFSCSFSPGLPRHRAL RTAPIQPRVWEPVPLEEVQLVVEPEG-GAVAPGGTVTLTCEVPAQPSPQIHWMKDG VPLPLPPSPVLILPEIGPQDQGTYSC-VATHSSHGPQESRAVSISIIEPGEEGPTA GSVGGSGLGTLALAPRGPTIKPCPPCK-CPAPNLLGGPSVFIFPPKIKDVLMISLS PIV-TCVVVDVSEDDPDVQISWFVNNVEVHTAQTQ-THREDYNSTLRVVSALPIQHQ DWMSGKEFKCKVNNKDLPAPIER-TISKPKGSVRAPQVYVLPPPEEEMTKKQVTLT CMVTDFMPEDIYVEWTNNGK-TELNYKNTEPVLDSDGSYFMYSKLRVEK-KNWVERN SYS-CSVVHEGLHNHHTTKSFSRTPGK

Representative RAGE peptides further include peptides derived from the N-terminus of RAGE, e.g., the C-domain and multimerization epitope, as disclosed in US2010/0226915A1.

Representative antibodies of the invention include antibodies that specifically bind RAGE and compete for binding to RAGE with an XT-H1, XT-H2, XT-H3, XT-H5, XT-H7, or XT-M4 antibody, or which bind to an epitope of RAGE bound by an XT-H1, XT-H2, XT-H3, XT-H5, XT-H7, or XT-M4 antibody, as disclosed in WO2007/109747.

Representative antibodies further include anti-RAGE antibodies that bind to various domains in RAGE. For example, antibodies that bind to the C1- and C2-domain in RAGE and compete with ligands, e.g., Aβ for binding to RAGE as disclosed in WO 2009/136382; antibodies that bind to the V-domain in RAGE and compete with ligands, e.g., S100b, HMGB1 and amyloid αβ for binding to RAGE, as disclosed in WO2007/109749; and antibodies that inhibit the interaction of human RAGE and a complex of HMGB1 and CpG DNA, as disclosed in WO2008/137552.

Antibodies that specifically bind to RAGE suitable for use in the methods of the invention also include variants of any of the antibodies described herein, which may be readily prepared using known molecular biology and cloning techniques. See, e.g., U.S. Published Patent Application Nos. 2003/0118592, 2003/0133939, 2004/0058445, 2005/0136049, 2005/0175614, 2005/0180970, 2005/0186216, 2005/0202012, 2005/0202023, 2005/0202028, 2005/0202534, and 2005/0238646, all of which are hereby incorporated by reference herein in their entireties.

In particular embodiments, antibodies that specifically bind to RAGE suitable for use in the methods of the invention specifically bind to the V domain of RAGE. In certain embodiments, the antibodies bind to a functional site on RAGE, such as residues 23-54 of RAGE. In particular embodiments, the antibodies specifically bind to the V-domain of RAGE and compete with ligands S100A7, S100A8, or S100A9.

Suitable antibodies may also comprise a label attached thereto, such as a detectable label (e.g., a radioisotope, fluorescent compound, enzyme or enzyme co-factor). Suitable antibodies include whole antibodies and fragments thereof including chimeric antibodies, humanized antibodies, single chain antibodies, tetrameric antibodies, tetravalent antibodies, heteroconjugate antibodies, bispecific antibodies, multispecific antibodies, domain-specific antibodies, domain-deleted antibodies, diabodies, antibody conjugates (e.g., with an Fc domain (e.g., an antigen binding domain fused to an immunoglobulin constant region), PEG, an immunoglobulin domain, etc.), Fab fragments, Fab' fragments, F(ab')$_2$ fragments, Fv fragments, ScFv fragments, Fd fragments, single domain antibodies, and dAb fragments, and Fc fusion protein.

In certain embodiments, an effective dose of the compound increases myofibrillar protein content and does not inhibit cellular proliferation of the myocyte. In certain embodiments, the myofibrillar protein is selected from myosin, actin, tropomyosin, myosin heavy chain, myosin light chain, troponin, titin, and nebulin. In a preferred embodiment, the myofibrillar protein is a myosin heavy chain protein.

In certain embodiments, the patient has cachexia-associated and/or RAGE cardiac dysfunction. Significantly, no treatment for cachexia-induced cardiac dysfunction was previously available.

In other embodiments, the patient has a cardiac dysfunction (e.g., congestive heart failure) or a disease-associated or disease-induced cachexia that is characterized by an increase in one or more S100 RAGE ligands (particularly, S100A7, S100A8, and S100A9) and/or a decrease in soluble RAGE relative to a reference level. In some embodiments, the patient has cachexia-associated cardiac dysfunction. In some other embodiments, the patient has cachexia-independent cardiac dysfunction.

In other embodiments, the patient has a cardiac dysfunction (e.g., congestive heart failure) or a disease-associated or disease-induced cachexia that is not associated with cancer, but that like cancer-induced cachexia fails to respond to treatment with nutritional support and anti-inflammatory therapy. T cardiac dysfunction may or may not be associated with cachexia. Like cancer-induced cachexia, the cardiac dysfunction can be characterized by an increase in one or more S100 RAGE ligands (particularly, S100A7, S100A8, and S100A9) and/or a decrease in soluble RAGE relative to a reference level.

In one embodiment, the invention provides a method of monitoring treatment progress. The method includes the step of determining a level of a cardiac dysfunction marker (e.g., levels of S100A7, S100A8, or S100A9) or diagnostic measurement (e.g., screen, assay) in a subject suffering from or susceptible to a disorder or symptoms thereof associated with a cardiac disease or dysfunction, in which the subject has been administered a therapeutic amount of a composition herein sufficient to treat the disease or symptoms thereof. The level of a cardiac dysfunction marker determined in the method can be compared to known levels of the cardiac dysfunction marker in either healthy normal controls or in other afflicted patients to establish the subject's disease status. In particular embodiments, a second level of a cardiac dysfunction marker in the subject is determined at a time point later than the determination of the first level, and the two levels are compared to monitor the course of disease or the efficacy of the therapy. In certain embodiments, a pre-treatment level of a cardiac dysfunction marker in the subject is determined prior to beginning treatment according to this invention; this pre-treatment level of the cardiac dysfunction marker can then be compared to the level of the marker in the subject after the treatment commences, to determine the efficacy of the treatment.

In some embodiments, a subject identified as having increased level of a S100 ligand, such as S100A7, S100A8, and/or S100A9, relative to a reference is administered a therapeutic composition of the invention. Levels of cardiac dysfunction markers (e.g., S100A7, S100A8, or S100A9) are measured in a subject sample and used as an indicator of a cardiac dysfunction that is responsive to treatment with an anti-RAGE agent (e.g., anti-RAGE antibody) of the invention. Levels of cardiac dysfunction marker polynucleotides may be measured by standard methods, such as quantitative PCR, Northern Blot, microarray, mass spectrometry, and in situ hybridization. Standard methods may be used to measure levels of cardiac dysfunction marker polypeptides in a biological sample derived from a subject. Such methods include immunoassay, ELISA, western blotting using an antibody that binds the marker polypeptide, and radioimmunoassay. Elevated levels of cardiac dysfunction marker polynucleotides or polypeptides are considered a positive indicator of cardiac dysfunction (particularly, cachexia-associated and/or RAGE-associated cardiac dysfunction) that is responsive to treatment with an anti-RAGE agent (e.g., anti-RAGE antibody) of the invention.

Pharmaceutical Compositions

The present invention features compositions useful for treating a cardiac dysfunction, particularly cachexia-associated cardiac dysfunction, in a subject. In some embodiments, the composition comprises an anti-RAGE agent, such as an anti-RAGE antibody, as described herein.

The administration of a composition comprising an anti-RAGE agent herein for the treatment of a cardiac dysfunction such as cachexia-associated or RAGE-associated cardiac dysfunction may be by any suitable means that results in a concentration of the therapeutic that, combined with other components, is effective in ameliorating, reducing, or stabilizing the disease symptoms in a subject. The composition may be administered systemically, for example, formulated in a pharmaceutically-acceptable buffer such as physiological saline. Preferable routes of administration include, for example, subcutaneous, intravenous, interperitoneally, intramuscular, or intradermal injections that provide continuous, sustained levels of the agent in the patient. The amount of the therapeutic agent to be administered varies depending upon the manner of administration, the age and body weight of the patient, and with the clinical symptoms of the cardiac dysfunction or disease. Generally, amounts will be in the range of those used for other agents used in the treatment of cardiac dysfunction, although in certain instances lower amounts will be needed because of the increased specificity of the agent. A composition is administered at a dosage that ameliorates or decreases effects of the cardiac dysfunction or disease (e.g., atrophy, irregular heart beat) as determined by a method known to one skilled in the art.

The therapeutic anti-RAGE agent (e.g., anti-RAGE antibody, or an antigen-binding fragment thereof) may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active agent substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with an organ, such as the heart; (v) formulations that allow for convenient dosing, such that doses are administered, for example, once every one or two weeks; and (vi) formulations that target a disease using carriers or chemical derivatives to deliver the therapeutic agent to a particular cell type (e.g., heart cell). For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the agent in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates a cardiac dysfunction or disease, the composition may include suitable parenterally acceptable carriers and/or excipients. The active therapeutic agent(s) (e.g., an anti-RAGE agent described herein) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

In some embodiments, the composition comprising the active therapeutic (i.e., an anti-RAGE antibody herein) is formulated for intravenous delivery. As indicated above, the pharmaceutical compositions according to the invention may be in the form suitable for sterile injection. To prepare such a composition, the suitable therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the agents is only sparingly or slightly soluble in water, a dissolution enhancing or solubilizing agent can be added, or the solvent may include 10-60% w/w of propylene glycol or the like.

Combination Therapies

In some aspects, the invention features methods of treating a cardiac dysfunction in a subject, the methods comprising administering to the subject an effective amount of a composition comprising an anti-RAGE agent (e.g., an anti-RAGE antibody) as described herein. Optionally, an anti-cardiac disease therapeutic of the invention (e.g., an anti-RAGE antibody as described herein) may be administered in combination with any other standard anti-cardiac disease therapy; such methods are known to the skilled artisan and described in Remington's Pharmaceutical Sciences by E. W. Martin.

Antibodies

Antibodies that selectively bind a RAGE polypeptide or a RAGE ligand (e.g., S100A7, S100A8, S100A9) are useful in the methods of the invention. Binding to the RAGE polypeptide reduces RAGE biological activity as assayed by analyzing, for example, modulation of cachexia in a cell using a cachexia functional assay as described herein. Methods of preparing antibodies are well known to those of ordinary skill in the science of immunology. As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments $F(ab')_2$, and Fab. $F(ab')_2$, and Fab fragments that lack the Fc fragment of intact antibody, clear more rapidly from the circulation, and may have less non-specific tissue binding of an intact antibody (Wahl et al., *J. Nucl. Med.* 24:316-325 (1983). The antibodies of the invention comprise whole native antibodies, bispecific antibodies; chimeric antibodies; Fab, Fab', single chain V region fragments (scFv), fusion polypeptides, and unconventional antibodies.

In one embodiment, an antibody that binds a RAGE polypeptide is monoclonal. Alternatively, the anti-RAGE antibody is a polyclonal antibody. The preparation and use of polyclonal antibodies are known to the skilled artisan. The invention also encompasses hybrid antibodies, in which one pair of heavy and light chains is obtained from a first antibody, while the other pair of heavy and light chains is obtained from a different second antibody. Such hybrids may also be formed using humanized heavy and light chains. Such antibodies are often referred to as "chimeric" antibodies.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated an "F(ab')$_2$" fragment, retains both of the antigen binding sites of the intact antibody. Similarly, an antibody from which the Fc region has been enzymatically cleaved, or which has been produced without the Fc region, designated an "Fab'" fragment, retains one of the antigen binding sites of the intact antibody. Fab' fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to immunogenic epitopes.

Antibodies can be made by any of the methods known in the art utilizing RAGE, or immunogenic fragments thereof, as an immunogen. One method of obtaining antibodies is to immunize suitable host animals with an immunogen and to follow standard procedures for polyclonal or monoclonal antibody production. The immunogen will facilitate presentation of the immunogen on the cell surface. Immunization of a suitable host can be carried out in a number of ways. Nucleic acid sequences encoding a RAGE polypeptide or immunogenic fragments thereof, can be provided to the host in a delivery vehicle that is taken up by immune cells of the host. The cells will in turn express the receptor on the cell surface generating an immunogenic response in the host. Alternatively, nucleic acid sequences encoding a RAGE polypeptide, or immunogenic fragments thereof, can be expressed in cells in vitro, followed by isolation of the polypeptide and administration of the polypeptide to a suitable host in which antibodies are raised.

Alternatively, antibodies against a RAGE polypeptide may, if desired, be derived from an antibody phage display library. A bacteriophage is capable of infecting and reproducing within bacteria, which can be engineered, when combined with human antibody genes, to display human antibody proteins. Phage display is the process by which the phage is made to 'display' the human antibody proteins on its surface. Genes from the human antibody gene libraries are inserted into a population of phage. Each phage carries the genes for a different antibody and thus displays a different antibody on its surface.

Antibodies made by any method known in the art can then be purified from the host. Antibody purification methods may include salt precipitation (for example, with ammonium sulfate), ion exchange chromatography (for example, on a cationic or anionic exchange column preferably run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

Antibodies can be conveniently produced from hybridoma cells engineered to express the antibody. Methods of making hybridomas are well known in the art. The hybridoma cells can be cultured in a suitable medium, and spent medium can be used as an antibody source. Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition (e.g., Pristane).

Monoclonal antibodies (Mabs) produced by methods of the invention can be "humanized" by methods known in the art. "Humanized" antibodies are antibodies in which at least part of the sequence has been altered from its initial form to render it more like human immunoglobulins. Techniques to humanize antibodies are particularly useful when non-human animal (e.g., murine) antibodies are generated. Examples of methods for humanizing a murine antibody are provided in U.S. Pat. Nos. 4,816,567, 5,530,101, 5,225,539, 5,585,089, 5,693,762 and 5,859,205.

In other embodiments, the invention provides "unconventional antibodies." Unconventional antibodies include, but are not limited to, nanobodies, linear antibodies (Zapata et al., Protein Eng. 8(10): 1057-1062, 1995), single domain antibodies, single chain antibodies, and antibodies having multiple valencies (e.g., diabodies, tribodies, tetrabodies, and pentabodies). Nanobodies are the smallest fragments of naturally occurring heavy-chain antibodies that have evolved to be fully functional in the absence of a light chain. Nanobodies have the affinity and specificity of conventional antibodies although they are only half of the size of a single chain Fv fragment. The consequence of this unique structure, combined with their extreme stability and a high degree of homology with human antibody frameworks, is that nanobodies can bind therapeutic targets not accessible to conventional antibodies. These multimeric scFvs (e.g., diabodies, tetrabodies) offer an improvement over the parent antibody since small molecules of ~60-100 kDa in size provide faster blood clearance and rapid tissue uptake: See Power et al., (Generation of recombinant multimeric antibody fragments for tumor diagnosis and therapy. Methods Mol Biol, 207, 335-50, 2003); and Wu et al. (Anti-carcinoembryonic antigen (CEA) diabody for rapid tumor targeting and imaging. Tumor Targeting, 4, 47-58, 1999).

Various techniques for making unconventional antibodies have been described. Bispecific antibodies produced using leucine zippers are described by Kostelny et al. (J. Immunol. 148(5):1547-1553, 1992). Diabody technology is described by Hollinger et al. (Proc. Natl. Acad. Sci. USA 90:6444-6448, 1993). Another strategy for making bispecific antibody fragments by the use of single-chain Fv (sFv) diners is described by Gruber et al. (J. Immunol. 152:5368, 1994). Trispecific antibodies are described by Tutt et al. (J. Immunol. 147:60, 1991). Single chain Fv polypeptide antibodies include a covalently linked VH::VL heterodimer which can be expressed from a nucleic acid including $V_H$- and $V_L$-encoding sequences either joined directly or joined by a peptide-encoding linker as described by Huston, et al. (Proc.

Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754.

Methods of Identifying Agents that Inhibit Cachexia and/or RAGE-Mediated Cachectogenic Signaling In Silico Drug Design The present invention permits the use of virtual design techniques (i.e., computer modeling or "in silico") to design, select, and synthesize compounds capable of regulating RAGE, in particular, RAGE-mediated cachetogenic signaling. In turn, these compounds may be effective in the treatment of a RAGE-regulated disorder, such as RAGE-associated cardiac dysfunction, cachexia, or a cachexia-associated disorder (e.g., a cachexia-associated cardiac dysfunction).

In addition to the more traditional sources of test compounds, computer modeling and searching technologies permit the rational selection of test compounds by utilizing structural information from the ligand binding sites and functional antibody binding sites (e.g., binding sites of cachexia-inhibitory antibodies) on proteins of the present invention (e.g., RAGE). Such rational selection of compounds may decrease the number of compounds that may need to be screened to identify a therapeutic candidate compound. In some embodiments, the functional site on RAGE comprises any one or more of amino acid residues 23-54 of RAGE. In some other embodiments, the functional site comprises any one or more amino acid residues 25, 54, 59, 61, 91, 92, 94, 96, 98, 114, 116, 150, 151, 152, 154, 175, 177, 178, 179, 186, 213, and 216 of RAGE.

Knowledge of the protein sequences of the present invention may allow for generation of models of their binding sites that may be used to screen for potential agent(s) that bind to the binding sites. This process may be accomplished with the skills known in the art. One approach involves generating a sequence alignment of the protein sequence to a template (derived from the crystal structures or NMR-based model of a similar protein(s)), conversion of the amino acid structures and refining the model by molecular mechanics and visual examination. If a strong sequence alignment may not be obtained, then a model may also be generated by building models of the hydrophobic helices. Mutational data that point towards contact residues may also be used to position the helices relative to each other so that these contacts are achieved. During this process, docking of the known ligands into the binding site cavity within the helices may also be used to help position the helices by developing interactions that may stabilize the binding of the ligand. The model may be completed by refinement using molecular mechanics and loop building using standard homology modeling techniques. General information regarding modeling may be found in Schoneberg, T. et. al., *Molecular and Cellular Endocrinology,* 151:181-193 (1999), Flower, D., *Biochim Biophys Acta,* 1422, 207-234 (1999), and Sexton, P. M., *Curr. Opin. Drug Discovery and Development,* 2, 440-448 (1999).

Once the model is completed, it may be used in conjunction with one of several computer programs to narrow the number of compounds to be screened, e.g., the DOCK program (UCSF Molecular Design Institute, San Francisco, Calif. 94143) or FLEXX (Tripos Inc., MO). One may also screen databases of commercial and/or proprietary compounds for steric fit and rough electrostatic complementarity to the binding site. In one embodiment, the docking program is ZDOCK (Pierce et al., *Bioinformatics.* 2014 Jun. 15; 30(12):1771-3). In another embodiment, the docking program is AutoDock Vina (Trott et al., *Journal of Computational Chemistry* 31 (2010) 455-461).

In Silico Screening of Compounds

In one aspect, the invention provides means to carry out virtual screening of compounds using the disclosed atomic coordinates or coordinates derived therefrom. The atomic coordinates of the three-dimensional structure elucidated by the invention are input into a computer so that images of the structure and various parameters are shown on the display. The resultant data are input into a virtual compound library. Since a virtual compound library is contained in a virtual screening software, the above-described data may be input into such a software. Compounds may be searched for, using a three-dimensional structure database of virtual or non-virtual compounds, such as MDDR (Prous Science, Spain).

The potential interactions of a compound may be analyzed prior to its actual synthesis and testing by the use of computer modeling techniques. If the theoretical structure of the given compound suggests insufficient interactions with RAGE, synthesis and testing of the compound may be obviated. However, if computer modeling indicate sufficient interactions, the molecule may then be synthesized and tested for its ability to regulate RAGE, using various methods described herein and/or that are known to a person skilled in the art. In one embodiment, the molecule is tested for its ability to modulate cachexia using the cachexia functiona assay described herein.

Compounds may be computationally evaluated and designed by means of a series of steps in which chemical entities or fragments are screened and selected for their ability to bind with individual binding sites or combinations thereof (e.g., P0, P+1, P-1) or other areas of RAGE.

One skilled in the art may use any of several methods to screen chemical entities or fragments for their ability to bind to RAGE and more particularly with the specific binding sites or functional sites described herein. Sequences of RAGE, may also be threaded onto the protein backbone of a RAGE domain (e.g., V domain, or any of the functional sites on RAGE described herein) derived from the crystal structure, with side chain positions optimized using methods known in the art. The resulting structural models may then be used to discover chemical entities or fragments that regulate RAGE via in silico docking. The process may begin by visual inspection of, for example, the functional site on the computer screen based on the RAGE coordinates presented in Protein Data Bank PDB ID 4LP4 (provided in Appendix A). Selected fragments or chemical entities may then be positioned in a variety of orientations, or docked, within a binding site of RAGE. Docking may be accomplished using software such as QUANTA™, SYBYL™, followed by energy minimization and molecular dynamics with molecular mechanics forcefields softwares, such as CHARMM™ and AMBER™.

Specialized computer programs may also assist in the process of selecting fragments or chemical entities. These include, but are not limited to, GRID™ (Goodford, P. J., J. Med. Chem., 28, 849-857 (1985)); MCSS™ (Miranker, A. and M. Karplus, "Proteins: Structure, Function and Genetics, 11, 29-34 (1991)); (3) AUTODOCK™ (Goodsell, D. S. and A. J. Olsen, Proteins: Structure, Function, and Genetics, 8, 195-202 (1990; DOCK™ (Kuntz, I. D. et al., J. Mol. Biol., 161, pp. 269-288 (1982)); GLIDE™ (Schrodinger Inc.); FLEXX™ (Tripos Inc); (7) GOLD™ (Jones et al., J. Mol. Biol., 245, 43-53, 1995).

Once suitable chemical entities or fragments have been selected, they may be assembled in silico or synthesized into a single compound. Chemical syntheses may be carried out by methods known in the art. In silico assembly may proceed by visual inspection of the relationship of the fragments to each other on the three-dimensional image displayed on a computer screen in relation to the structure coordinates of RAGE. This may be followed by manual model building using softwares such as QUANTA™ or SYBYL™.

Useful programs for connecting the individual chemical entities or fragments include the following: CAVEAT™ (Bartlett, P. A. et al, Royal Chem. Soc., 78, 182-196 (1989)); 3D Database systems such as MACCS-3D™ (MDL Information Systems, San Leandro, Calif.); and HOOK™ (Molecular Simulations, Burlington, Mass.). In addition to building a compound in a step-wise fashion as described above, compounds may be designed as a whole or "de novo" using an empty active site or optionally including some portion(s) of a known compound. Such methods include, but are not limited to, LUDI™ (Bohm, H.-J., J. Com R. Aid. Molec. Design, 6, pp. 61-78 (1992)); LEGEND™ (Nishibata, Y. and A. Itai, Tetrahedron, 47, p. 8985 (1991)), and LEAP-FROG™ (Tripos Inc., St. Louis, Mo.).

Once a compound has been designed or selected, the efficiency with which that compound may regulate RAGE may be tested and optimized by computational evaluation. For example, a compound may demonstrate a relatively small difference in energy between its bound and unbound states (i.e., a small deformation energy of binding). A compound may interact with RAGE in more than one conformation that is similar in overall binding energy. In those cases, the deformation energy of binding is taken to be the difference between the energy of the unbound compound and the average energy of the conformations observed.

A compound that is designed or selected may be further computationally optimized so that in its bound state it may lack repulsive electrostatic interactions. Such interactions include repulsive charge-charge, dipole-dipole, and charge-dipole interactions. The sum of all electrostatic interactions between the compound and RAGE, may make a neutral or favorable contribution to the enthalpy of binding. Software programs to evaluate compound deformation energy and electrostatic interaction include, e.g., Gaussian 92™ (M. J. Frisch, Gaussian, Inc., Pittsburgh, Pa.); AMBER™ (P. A. Kollman, University of California at San Francisco, Calif.); QUANTA/CHARM™ (Molecular Simulations, Inc., Burlington, Mass.); and Insight II/Discover™ (Biosym Technologies Inc., San Diego, Calif.).

Once a compound has been optimally selected or designed, substitutions may be made in some of its atoms or side groups in order to improve or modify its binding properties. Initial substitutions may be conservative, i.e., the replacement group will have approximately the same size, shape, hydrophobicity and charge as the original group. Such substituted compounds may then be analyzed for efficiency of fit to RAGE by software programs similar to those described.

Crystallographic Evaluation of Chemical Entities for Binding to RAGE

The invention allows one skilled in the art to study the binding of compounds to RAGE by exposing either individual compounds or mixtures of compounds (such as may be obtained from combinatorial libraries) into RAGE crystals or, alternatively, by co-crystallization of the compounds of interest with RAGE, using methods known in the art, and those described in the Examples herein. Acquisition and analysis of X-ray diffraction data from these crystals may then be performed using standard methods. If a compound binds to RAGE then positive difference electron density will be observed in the Fourier maps calculated using the X-ray diffraction intensities and phases obtained from the RAGE model presented herein. Models of the chemical entities may then be built into the electron density using standard methods, and the resulting structures may be refined against the X-ray diffraction data, providing experimental data describing the interaction of the compounds of interest. Those skilled in the art may use these models to design compounds based either on purely structural data; or on combination of structural data, biological/chemical activity based structure-activity relationship, and in silico drug design.

The compounds that are thus designed or selected may further be tested in an in vitro, in vivo, or ex vivo assays to determine if they regulate RAGE. Such assays are known to one skilled in the art. In some embodiments, the assay is a cachexia functional assay as described herein and further described in PCT/US2014/068631, which is incorporated herewith in its entirety.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

Example 1

Identification of Functional Sites on RAGE Polypeptide

Figure 2:
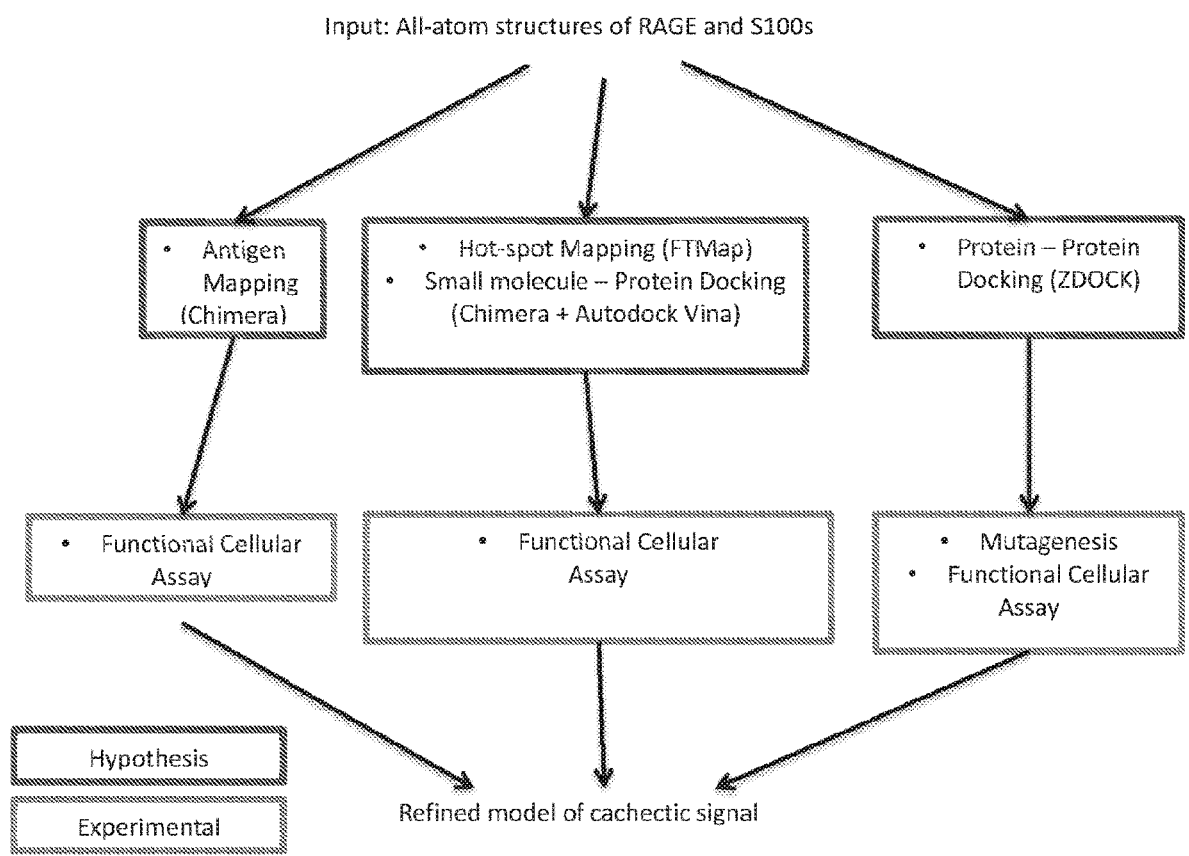
FIG. 2 is a diagram showing a methodology described herein for obtaining a refined model of the cachectic signal. The methodolgy combines computational modeling, hypothesis generation, and experimental verification of hypothesis and computational models.

In studies described herein below, a refined model of the cachectic signal was obtained (FIG. 2). Functional sites on the RAGE polypeptide were determined using a combination of experiments mapping binding interface(s) of anti-RAGE antibodies with RAGE polypeptide using hydrogen-deuterium exchange (HDEX) reactions and cachexia functional assays. As described elsewhere herein, results of the cachexia functional assay indicate whether a candidate agent (e.g., a particular anti-RAGE antibody) has cachexia-inhibitory or cachexia-inducing activity, as measured, for example, by levels of myosin heavy chain in cells treated with the candidate agent relative to a control or baseline myosin heavy chain level.

Figure 4:
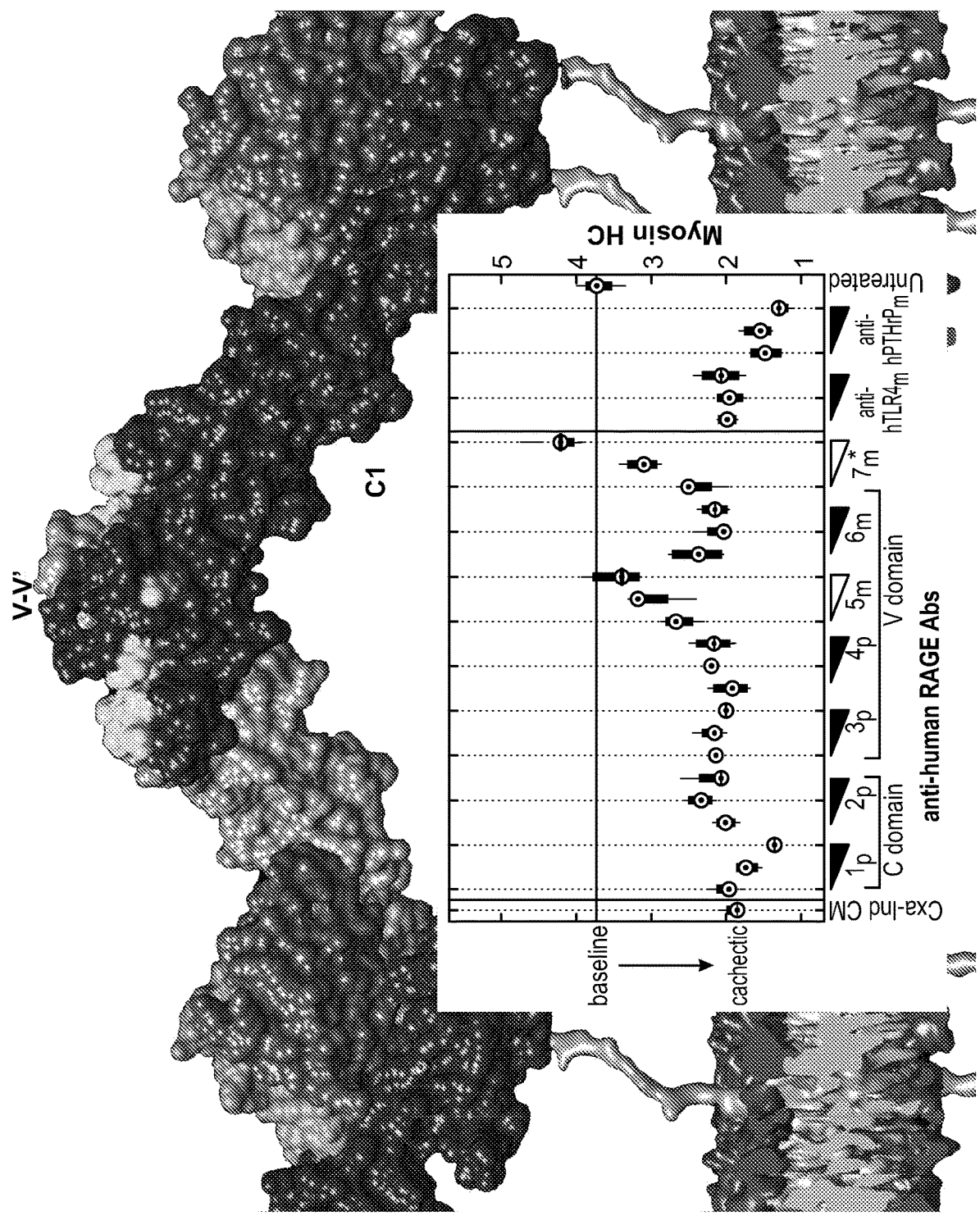
FIG. 4 provides a plot showing results of antigen mapping of various anti-RAGE antibodies. Using the cachexia functional assay as described herein, the plot indicates the effects the anti-RAGE antibody on cachexia as a function of the location or site on RAGE to which the antibody binds.
Figure 17:
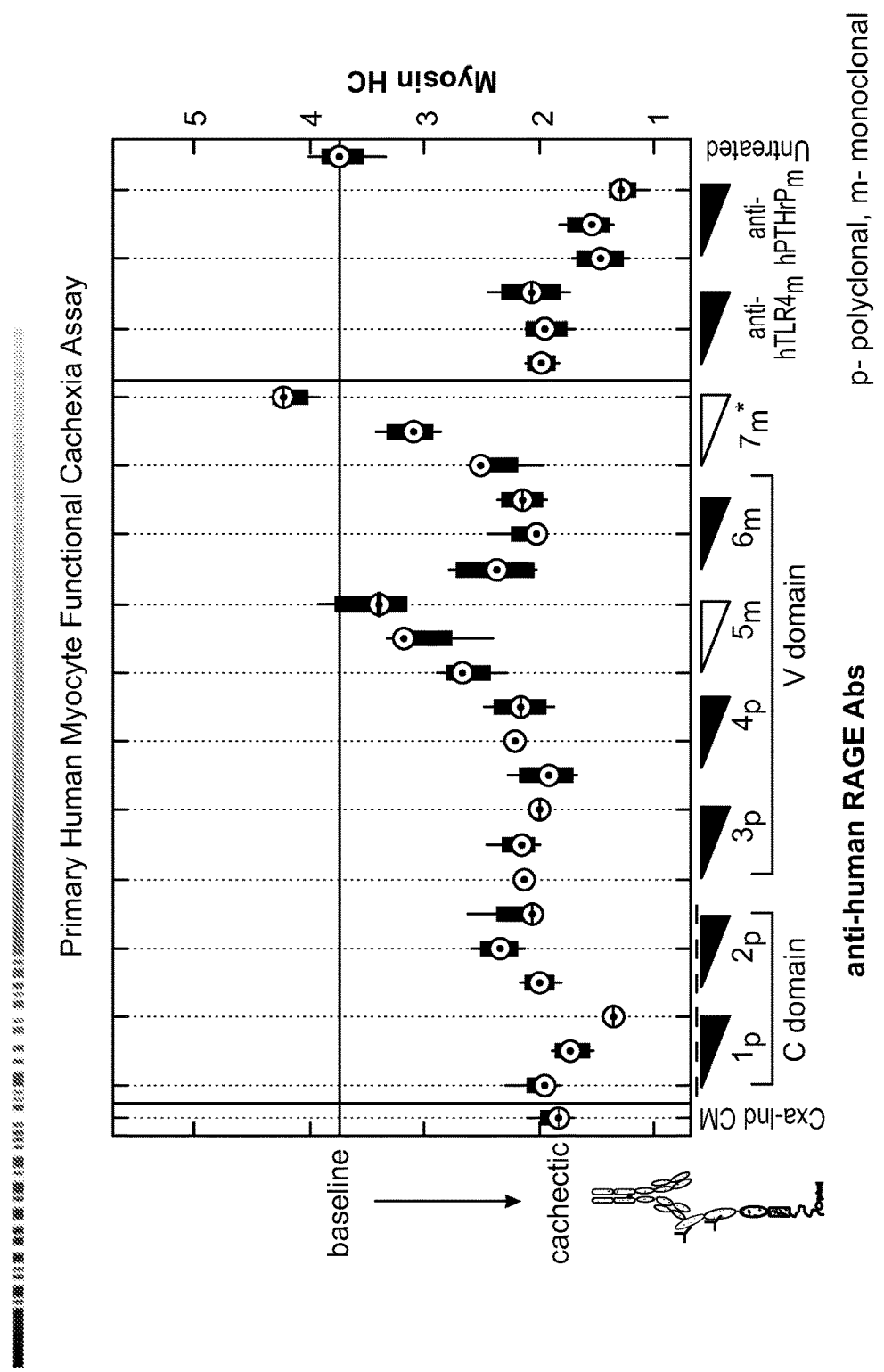
FIG. 17 is a plot showing antigen mapping of the RAGE polypeptide. The plot shows functional regions or functional sites on the RAGE polypeptide, based on results of the cachexia functional assay described herein. Sites highlighted in light gray, for example, are antigens of anti-RAGE antibodies that have a cachexia-inhibitory effect.
Figure 20:
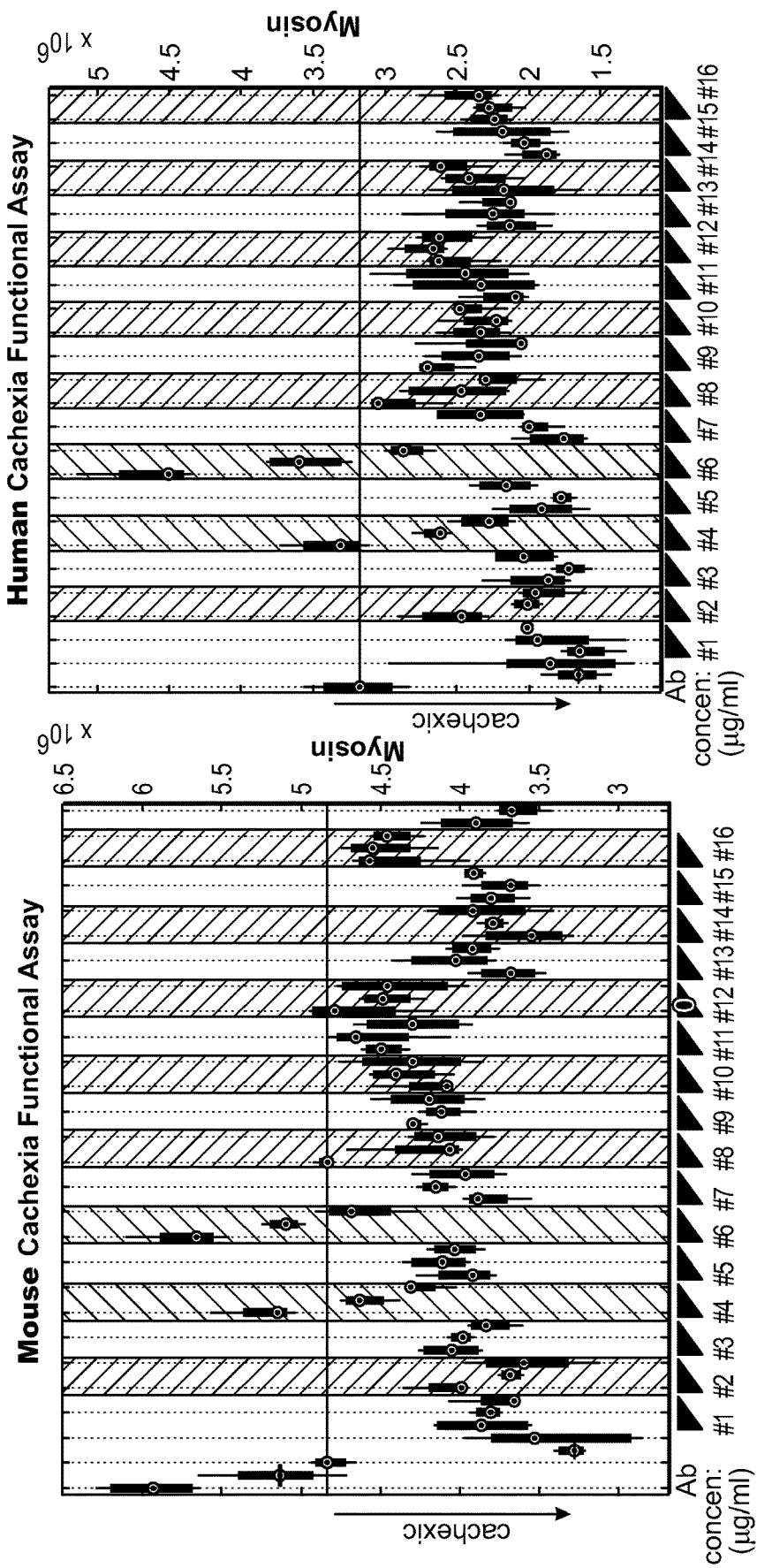
FIG. 20 is set of plots showing results of screening of anti-RAGE antibodies in a mouse cachexia functional assay (left) and human cachexia functional assay (right). Out of the 22 anti-RAGE antibody candidates screened, 2 antibodies were identified as anti-RAGE antibodies having cachexia-inhibitory activity.
Figure 21:
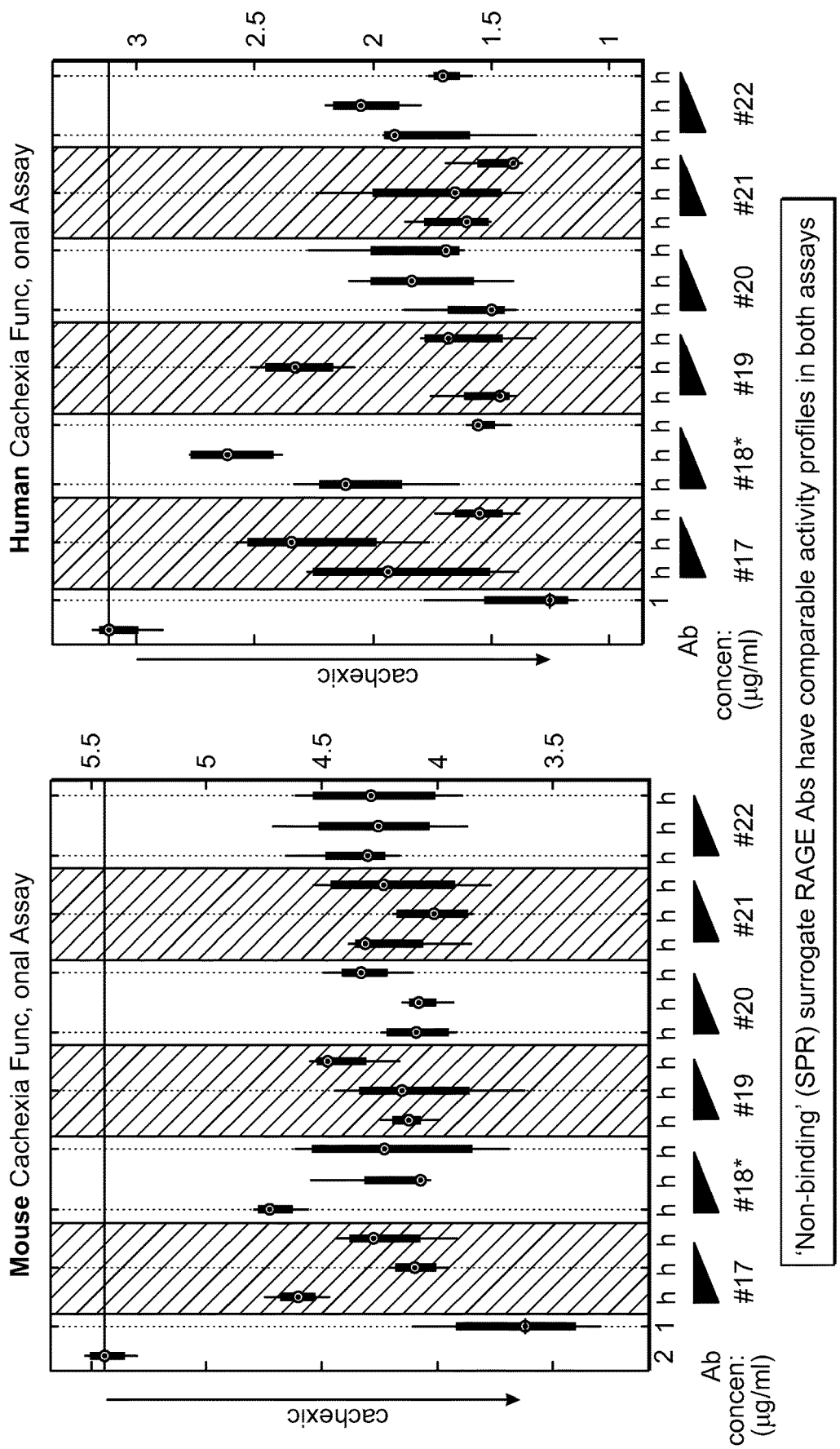
FIG. 21 is a set of plots showing that surrogate RAGE antibodies had comparable activity profiles in both mouse cachexia (left) and human cachexia (right) functional assays.

The anti-RAGE antibodies were found to bind to various sites on RAGE (FIG. 4; FIG. 17). Results of screening of anti-RAGE antibodies in a mouse cachexia functional assay (left) and human cachexia functional assay are shown in FIG. 20. Out of the 22 anti-RAGE antibody candidates screened, two (2) antibodies, were identified as anti-RAGE antibodies having cachexia-inhibitory activity (FIG. 22). FIG. 21 shows that surrogate RAGE antibodies had comparable activity profiles in both mouse cachexia (left) and human cachexia (right) functional assays.

Figure 5:
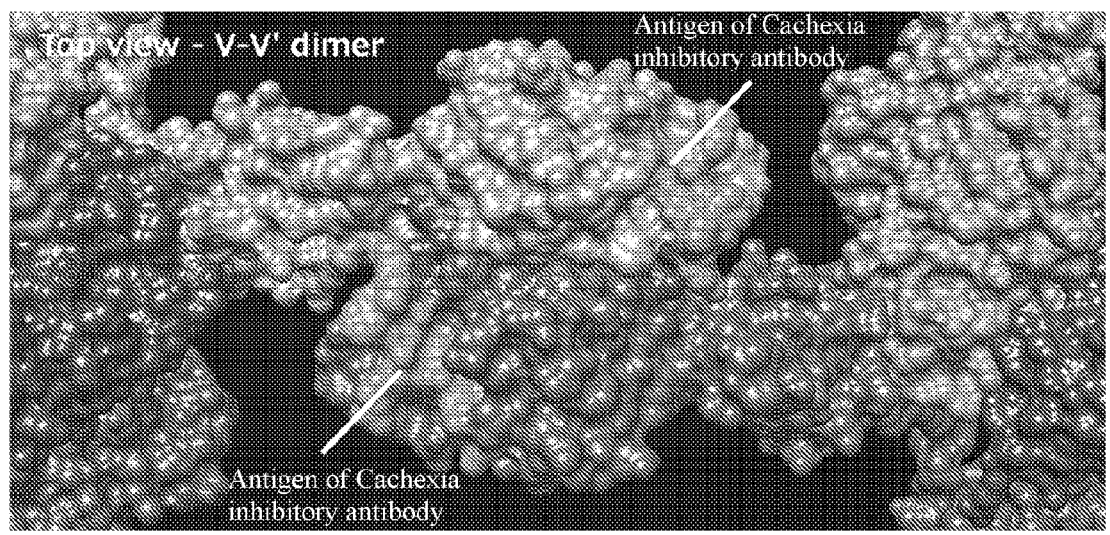
FIG. 5 provides a top view of the V domains of RAGE, which interact to form a dimer. The antigen of the cachexia inhibitory antibody is indicated.

Anti-RAGE antibodies having cachexia-inhibitory activity were found to bind to a particular site on the V domain of RAGE (residues 23-54). The antigen (or binding site) of the cachexia-inhibitory antibody on RAGE is shown in FIGS. 3A-3B and FIG. 5.

Figure 6B:
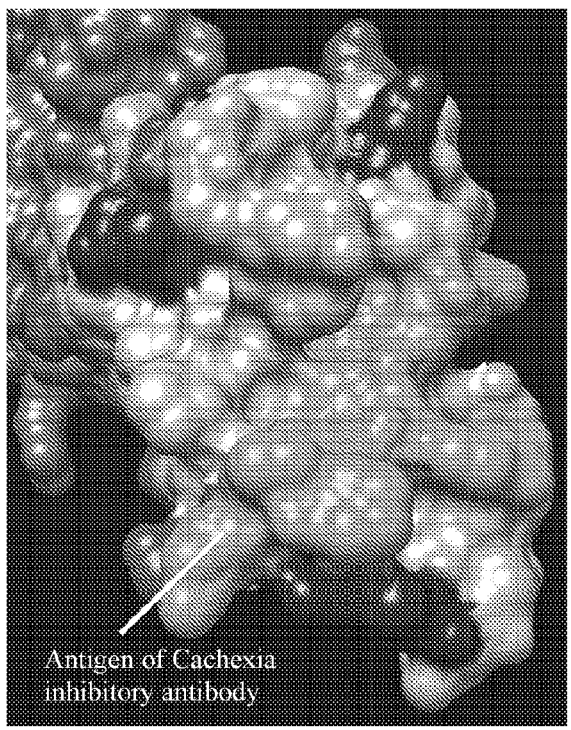
FIG. 6B is a schematic showing a magnified view of an end portion of the V domain of RAGE, indicated by the arrow in FIG. 6A. The antigen of the cachexia inhibitory antibody is indicated.
Figure 6C:
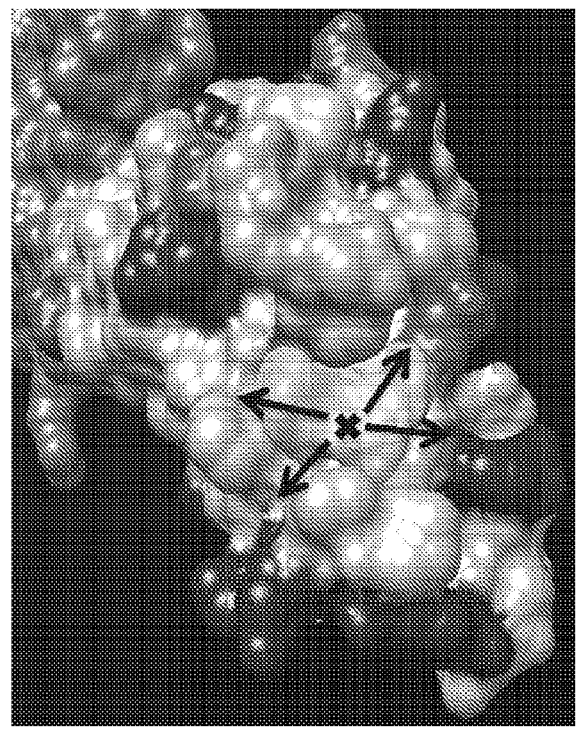
FIG. 6C is a schematic showing a magnified view of an end portion of the V domain of RAGE. A druggable "hot spot" is indicated by "X" and the arrows extending from the "X."

Based on these results, a druggable "hot spot" on the RAGE polypeptide was identified (FIGS. 6A-6C). Without being bound by theory, agents that bind to the hot spot are expected to inhibit RAGE-mediated cachectic signaling, thereby inhibiting cachexia in a cell or a subject. The "hot spot" is located on the V domain of RAGE and corresponds to the region marked with an "X" in FIG. 6C. Thus, the hot spot serves as a target site for rational drug design to identify agents that inhibit RAGE mediated-signaling and cachexia.

Figure 7A:
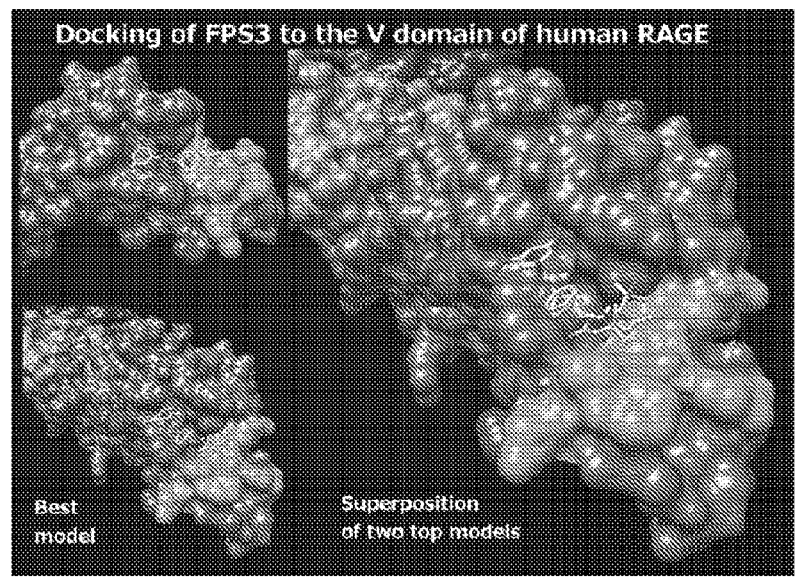
FIG. 7A is a series of schematics showing docking of an exemplary small molecule inhibitor of RAGE (FPS3) to the V domain of RAGE.
Figure 7B:
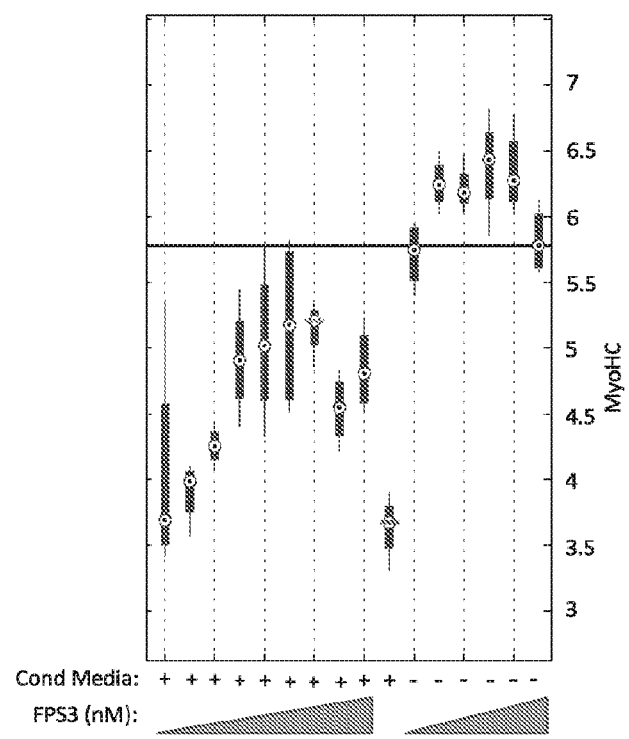
FIG. 7B is a plot showing results of the cachexia functional assay (i.e., levels of myosin heavy chain) as a function of concentration of FPS3.

FIG. 7A is a series of schematics showing docking of an exemplary small molecule inhibitor of RAGE (FPS3) to the hot spot of RAGE. Docking of FPS3 indicates a favorable fit of FPS3 within the hot spot. Results of a cachexia functional assay wherein cells were treated with various concentrations of FPS3 showed that FPS3 had cachexia-inhibitory activity (FIG. 7B).

Figure 8:
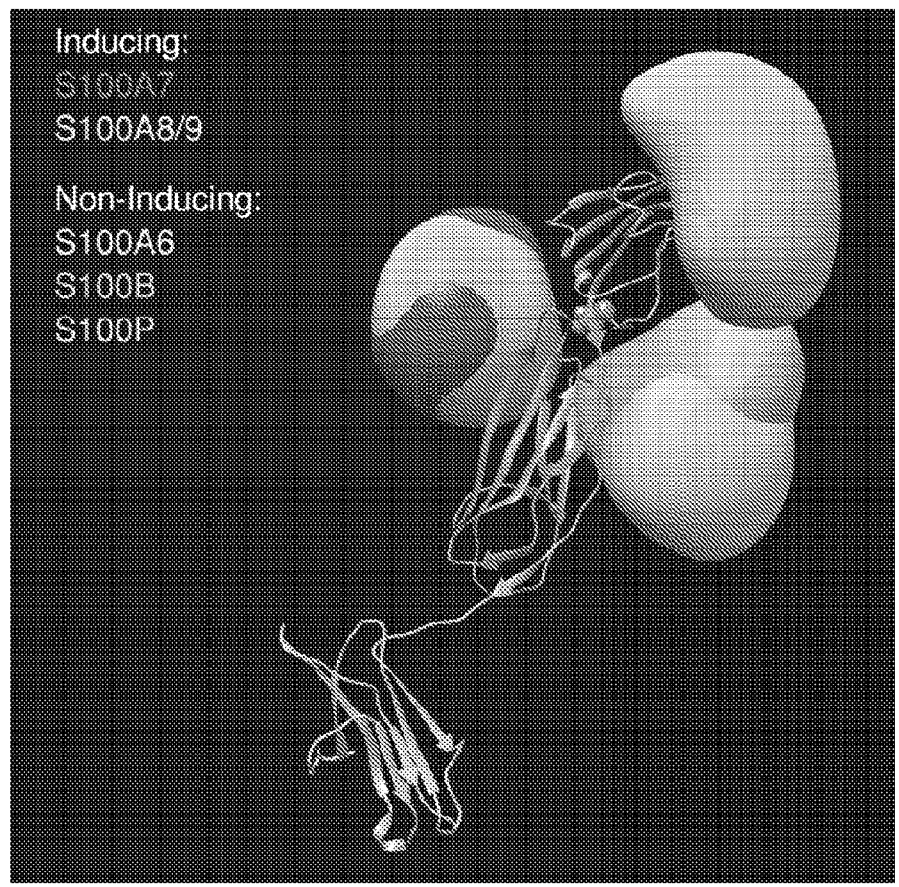
FIG. 8 is a schematic representation of RAGE polypeptide and its ligands, S100A7, S100A8/9, S100A6, S100B, and S100P, where S100A7 and S100A8/9 are cachexia-inducing and the remaining ligands are not cachexia-inducing.

In another set of experiments, the residues on ligands of RAGE that contact RAGE and the residues on RAGE that contact RAGE ligands were determined. FIG. 8 is shows RAGE polypeptide and its ligands, S100A7, S100A8/9, S100A6, S100B, and S100P. The ligands S100A7 and S100A8/9 are cachexia-inducing ligands, whereas the ligands S100A6, S100B, and S100P are non-cachexia-inducing ligands, as measured by the cachexia functional assay descibred herein.

Figure 9:
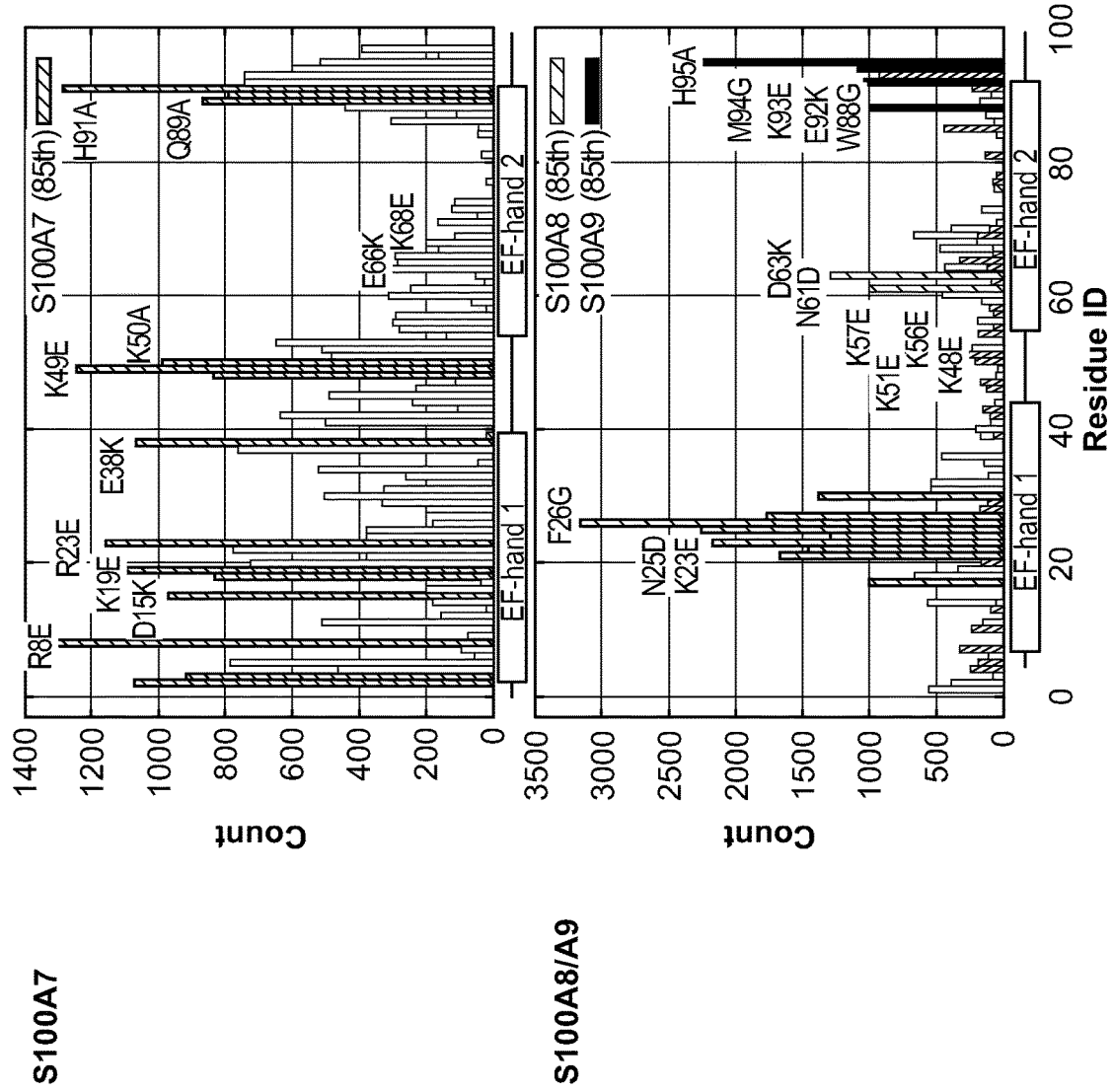
FIG. 9 is a series of plots and schematics showing residues on ligands S100A7 (top) and S100A8/A9 (bottom) which contact the RAGE polypeptide.
Figure 10:
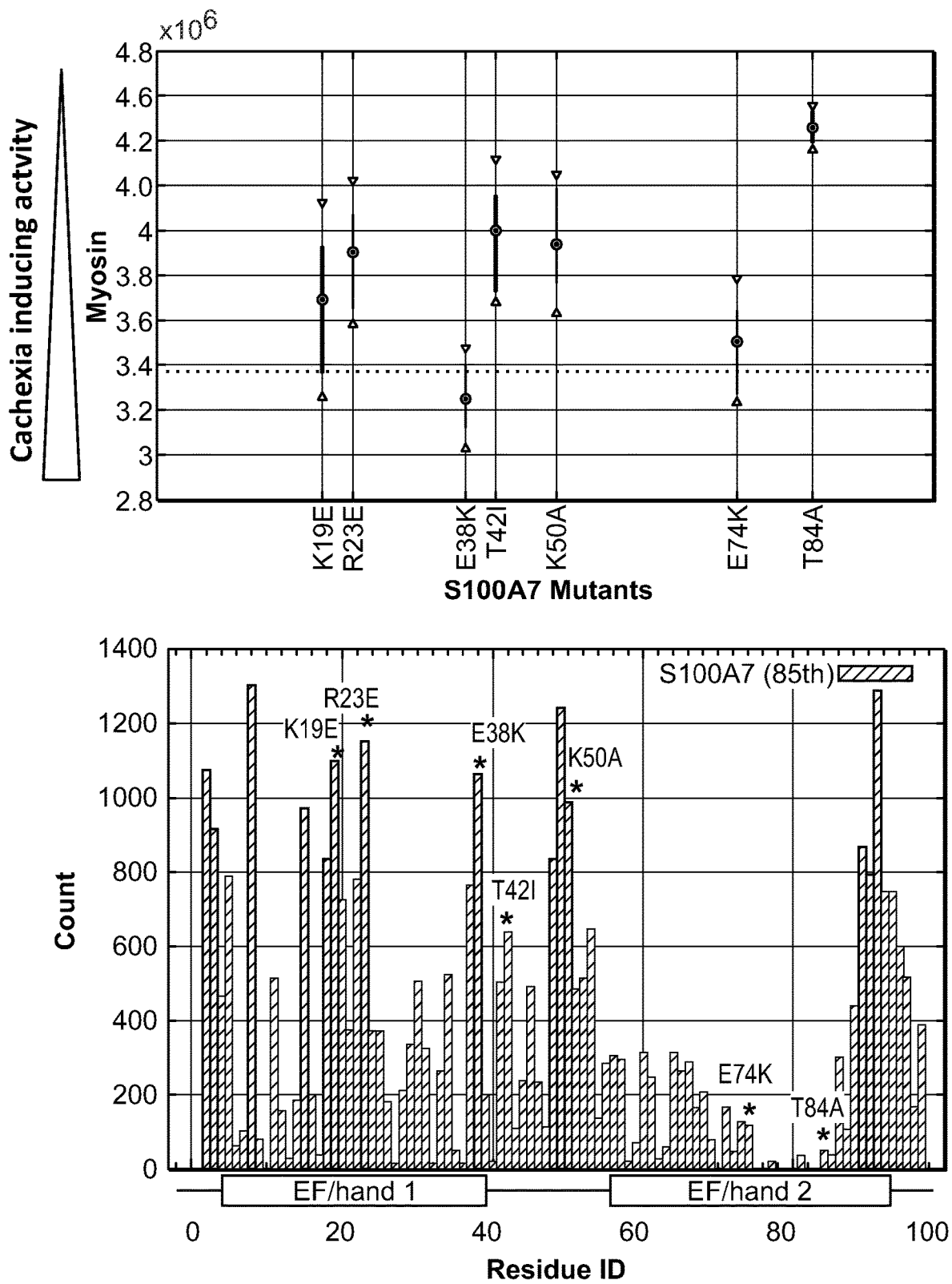
FIG. 10 is a set of plots showing mutagenesis of S100A7 and effects of the S100A7 mutants on cachexia using the cachexia functional assay described herein.

FIG. 9 shows residues on ligands S100A7 and S100A8/A9 which contact the RAGE polypeptide. The residues contacting RAGE on S100A7 were confirmed by mutagenesis of S100A7 and investigation of effects of the S100A7 mutants on cachexia using the cachexia functional assay described herein (FIG. 10).

Figure 11:
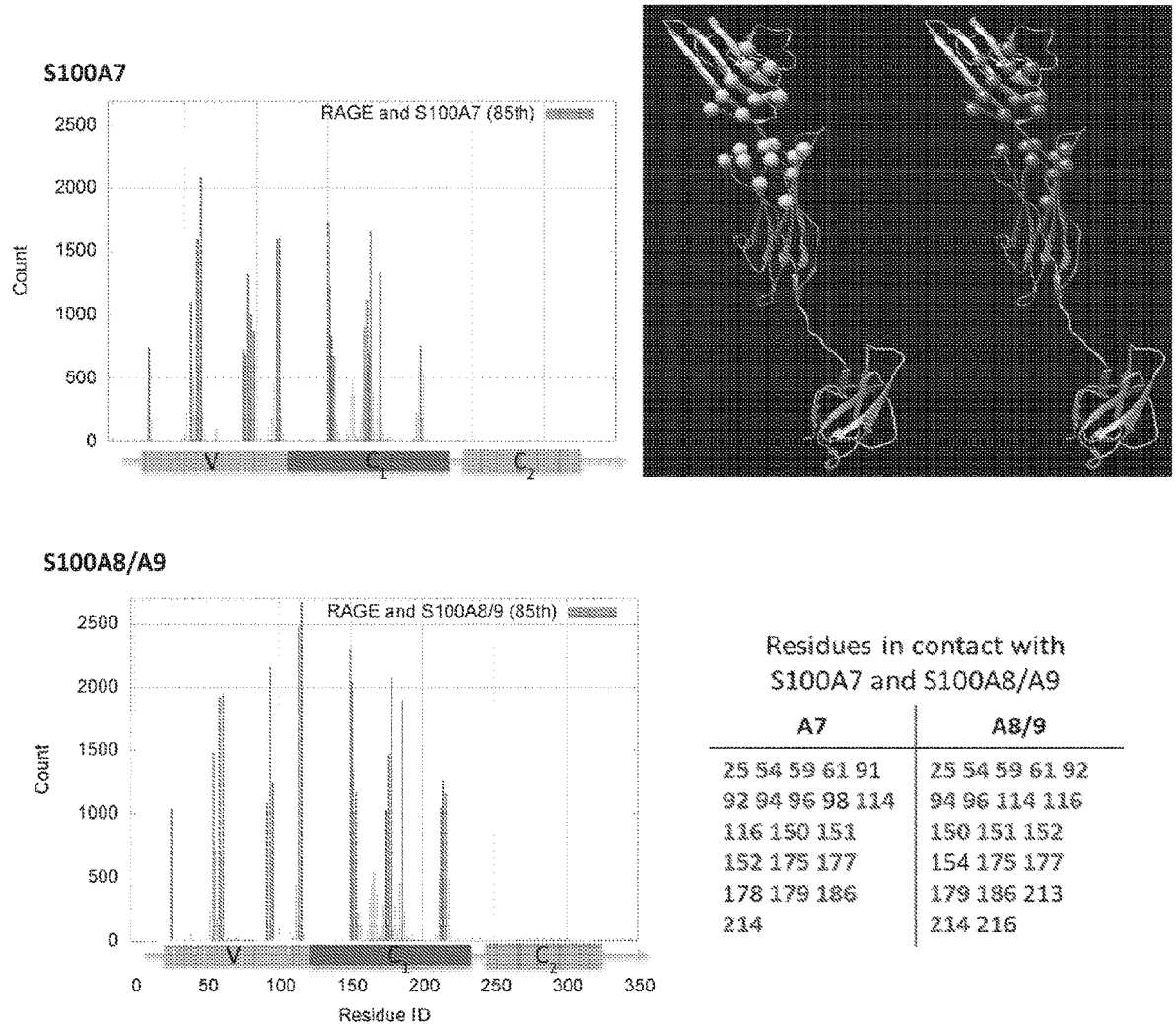
FIG. 11 is a series of plots and schematics showing residues on the RAGE polypeptide that contact S100A7 (top) and S100A8/A9 (bottom). Residues on RAGE that contact S100A7 and S100A8/A9 are listed in the table at the bottom right of FIG. 11.
Figure 18:
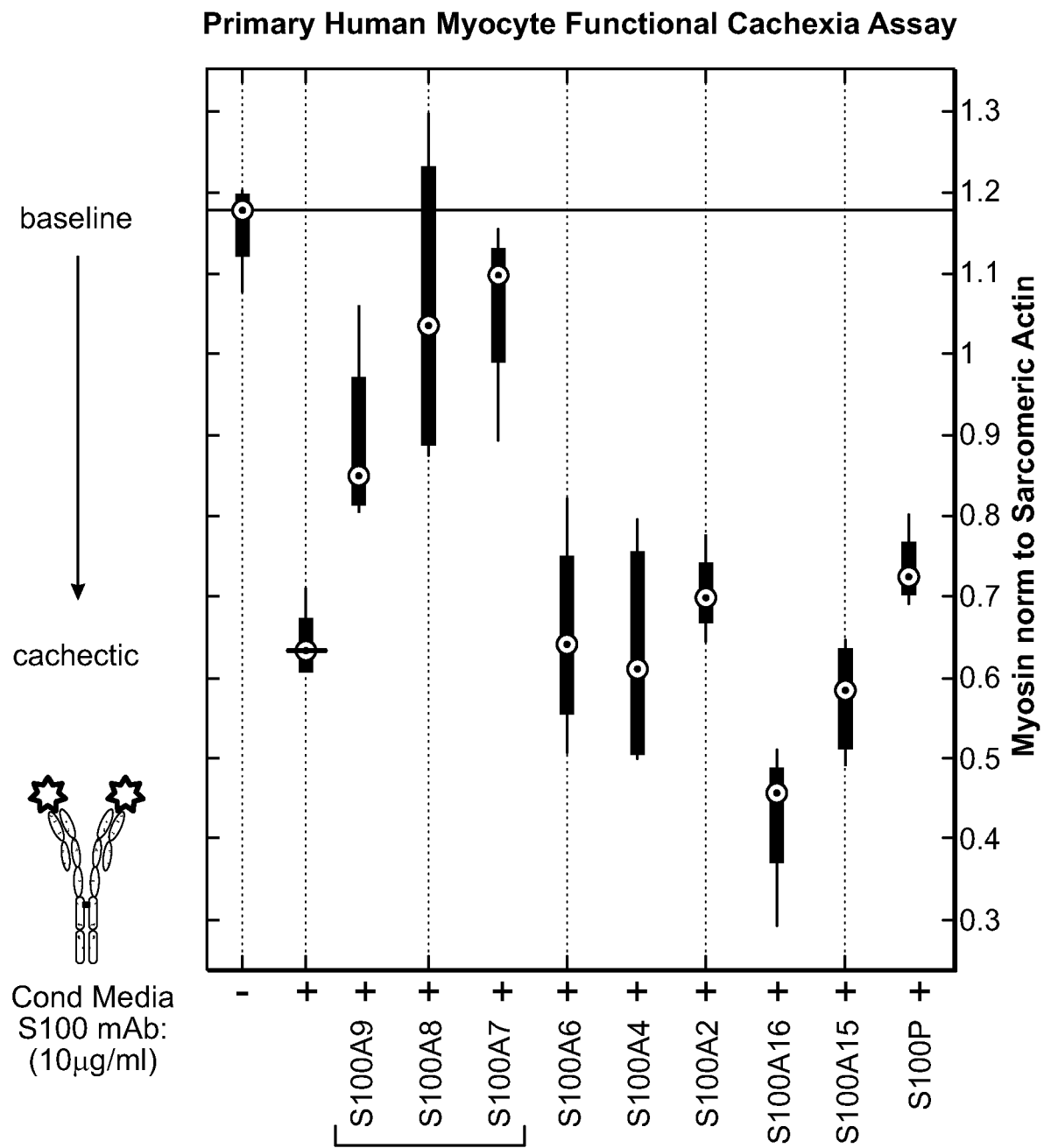
FIG. 18 is a plot showing that antibodies targeting cachexia-inducing ligands (S100A7, S100A8, S100A9) had cachexia-inhibiting activity.

FIG. 11 shows residues on the RAGE polypeptide that contact S100A7 and S100A8/A9 (cachexia-inducing ligands). Residues on RAGE that contact S100A7 and S100A8/A9 are listed in the table at the bottom right of FIG. 11. As shown in the table, the set of residues on RAGE that each of the cachexia-inducing ligands contact is nearly identical, indicating that the site on RAGE defined by these residues is a functional site that may be targeted to inhibit cachexia. Agents that block binding of S100A7 and/or S100A8/A9 to this site, for example, may inhibit cachexia. For example, agents that target S100A7 or S100A8/A9, such as antibodies against S100A7 or S100A8/A9, were found to inhibit cachexia (FIG. 18).

Figure 12:
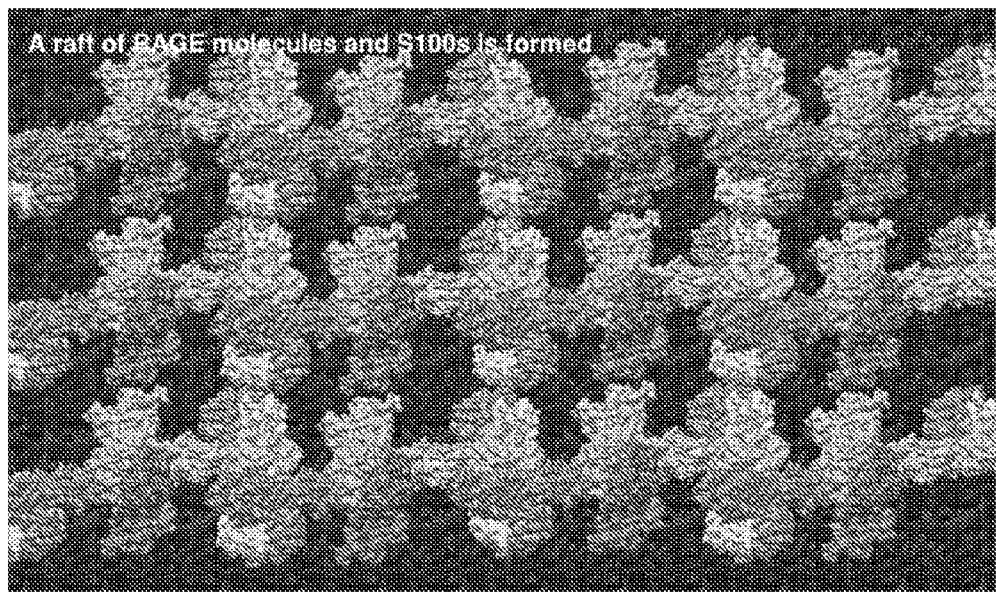
FIG. 12 is a schematic showing a multidimensional RAGE model predicting cachexogenic signaling. In the model, a raft of RAGE molecules and S100 ligands is formed.

FIG. 12 shows a multidimensional RAGE model predicting cachexogenic signaling. In the model, a raft of RAGE molecules and S100 ligands is formed. Without intending to be bound by theory, it is believed that disrupting the formation of the raft (e.g., by disruption of RAGE oligomerization and/or S100 ligand binding) disrupts cachexogenic signaling. Agents that bind to the "hot spot" of RAGE and/or block binding of S100A7 or S100A8/A9 to their binding site on RAGE are expected to disrupt cachexogenic signaling, thereby inhibiting cachexia.

Example 2

Prevention and Reversal of Cardiac Atrophy and Cardiac Dysfunction by Anti-RAGE Antibodies In another set of experiments, anti-RAGE antibodies were shown to prevent and reverse cardiac atrophy and cardiac dysfunction in a clinically relevant model of human cardiac function. A cardiac cachexia model was generated using cardiomyocytes differentiated from induced pluripotent stem cells (iPS cells) (FIG. 13). Assessment of gene expression, protein markers, and electrophysiology of the cardiomyocytes was performed. The cardiac model generated was found to exhibit molecular and functional characteristics of cardiac tissue (e.g., similar gene expression signature, synchronized beating) (FIG. 13).

Figure 14:
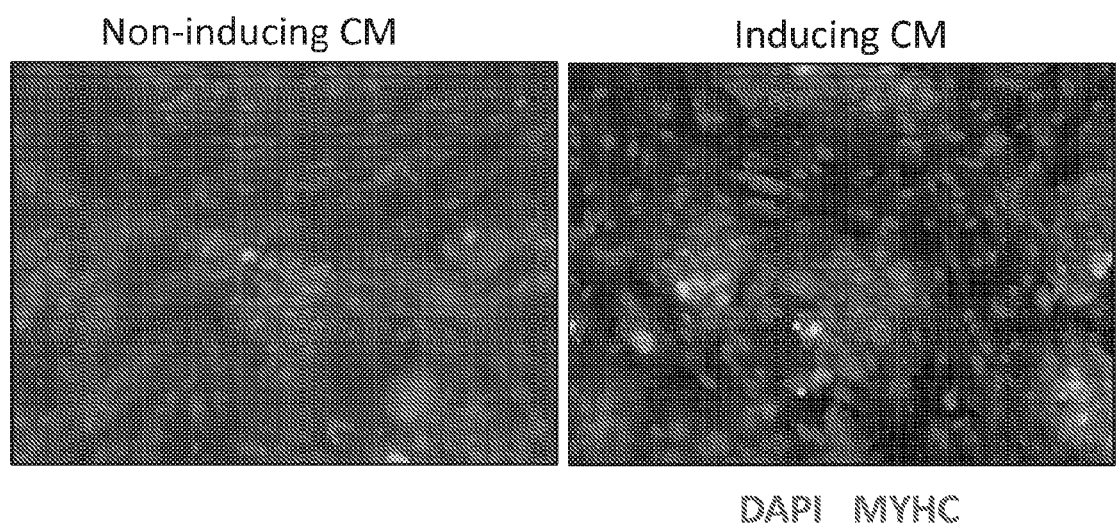
FIG. 14 is a set of micrographs showing cachexia-induced cardiac atrophy.

The cardiomyocytes were then treated or cultured in cachexia-inducing medium. FIG. 14 shows cachexia-induced cardiac atrophy. FIG. 14 shows a loss of myosin heavy chain in cardiomyocytes treated with a cachexia-inducing medium described herein (right) relative to cardiomyocytes not treated with cachexia-inducing medium (left).

Figure 15:
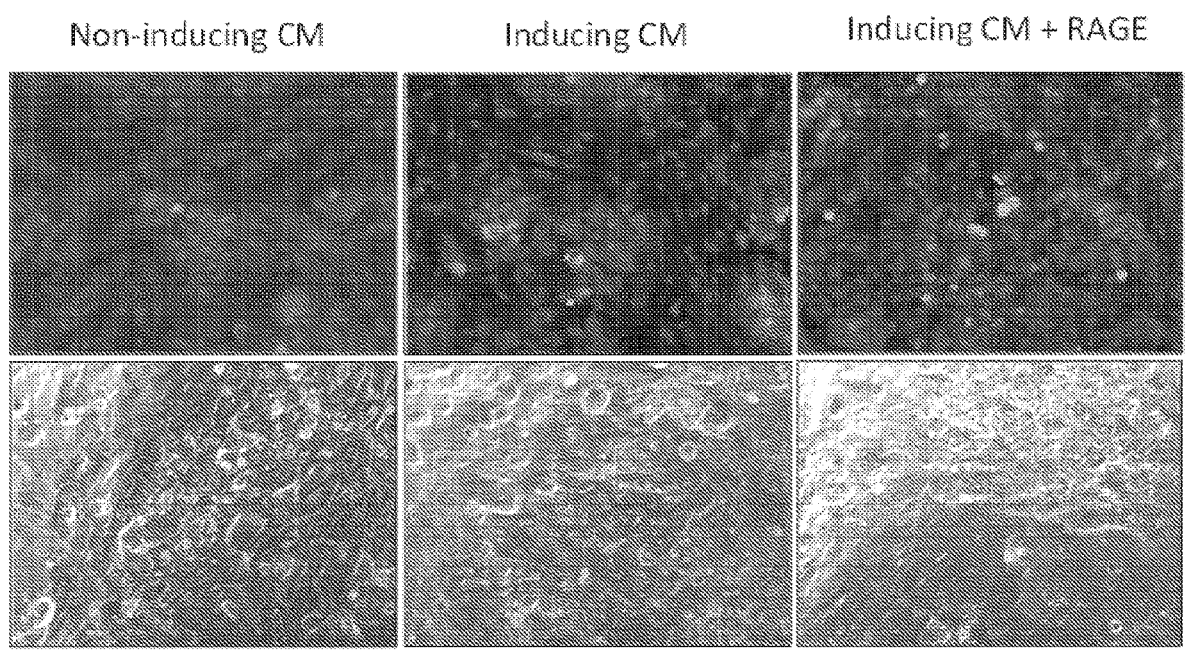
FIG. 15 is a set of micrographs showing cardiac atrophy and cardiac dysfunction is prevented by an anti-RAGE antibody. From left to right, the micrographs show cardiomyocytes treated with (1) non-inducing medium, (2) cachexia-inducing medium, and (3) cachexia-inducing medium and anti-RAGE antibody. The micrographs in the top panel show DAPI stained and myosin heavy chain (MYHC) stained cardiomyocytes. Light gray indicates myosin heavy chain (MYHC). The right-most micrograph at the top shows that the anti-RAGE antibody prevented or inhibited loss of myosin heavy chain in the cardiomyocytes. The micrographs in the bottom panel are from videomicrographs showing that (1) cardiac tissue in non-inducing medium exhibited a regular beat, (2) cardiac tissue in cachexia-inducing medium exhibited an irregular heart beat, and (3) cardiac tissue in cachexia-inducing with anti-RAGE antibody exhibited a regular heart beat, thus indicating that cardiac dysfunction was inhibited or prevented by the anti-RAGE antibody.

Next, the effect of anti-RAGE antibodies on cachexia-induced cardiac atrophy and cardiac dysfunction was investigated. FIG. 15 shows cardiac atrophy and cardiac dysfunction was prevented by an anti-RAGE antibody. From left to right, the micrographs show cardiomyocytes treated with (1) non-inducing medium, (2) cachexia-inducing medium, and (3) cachexia-inducing medium and anti-RAGE antibody. The micrographs in the top panel show DAPI stained and myosin heavy chain (MYHC) stained cardiomyocytes. Light gray indicates myosin heavy chain (MYHC). The right-most micrograph at the top shows that the anti-RAGE antibody prevented or inhibited loss of myosin heavy chain in the cardiomyocytes. The micrographs in the bottom panel are from videomicrographs showing that (1) cardiac tissue in non-inducing medium exhibited a regular beat, (2) cardiac tissue in cachexia-inducing medium exhibited an irregular heart beat, and (3) cardiac tissue in cachexia-inducing with anti-RAGE antibody exhibited a regular heart beat, thus indicating that cardiac dysfunction was inhibited or prevented by the anti-RAGE antibody.

FIG. 16 shows that cardiac atrophy and cardiac dysfunction were reversed by an anti-RAGE antibody. The micrographs on the left show DAPI stained and myosin heavy chain (MYHC) stained cardiomyocytes. On the left, the top micrograph shows loss of myosin heavy chain in cardiomyocytes treated with cachexia inducing medium. The bottom micrograph on the left shows myosin heavy chain restored in those cardiomyocytes after treatment with an anti-RAGE antibody. The micrograph on the right is a micrograph from a videomicrograph showing that regular heart beat was restored in cardiac tissue in cachexia-inducing medium following treatment of the cardiac tissue with anti-RAGE antibody. Thus, the results show that the loss of myosin heavy chain in cardiomyocytes was rescued by treatment with an anti-RAGE antibody.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method for synthesizing a candidate compound that binds to a site on a RAGE polypeptide, the method comprising:
(a) accessing, by a computer, a three-dimensional structure of a RAGE polypeptide having at least one atomic coordinate, or surrogate thereof, from Protein Data Bank (PDB) ID: 4LP4 for each of the amino acid residues 23-54 or for each of the amino acid residues 25, 54, 59, 61, 91, 92, 94, 96, 98, 114, 116, 150, 151, 152, 154, 175, 177, 178, 179, 186, 213 and 216 of the RAGE polypeptide, or having atomic coordinates that have a root mean square deviation of the coordinates of less than 3 angstroms;
(b) screening, by the computer, each chemical compound fragment in a set of chemical compound fragments having a three dimensional structure that interacts with the three-dimensional structure of the RAGE polypeptide accessed in step (a) by determining a subset of the chemical compound fragments in the set of the chemical compound fragments that have one or more different orientations of the three-dimensional structure of the subset of the chemical compound fragments that are complementary to a binding site of the three-dimensional structure of the RAGE polypeptide to structurally model a specific interaction of the with the binding site on the RAGE polypeptide;
(c) selecting, by the computer, a candidate compound structure comprising a selection of chemical compound fragments in the subset of the chemical compound fragments, wherein the selection of chemical compound fragments (i) specifically interact with a binding site of the RAGE polypeptide based on step (b), and/or (ii) possesses one or both of steric fit and electrostatic complementarity to the binding site of the RAGE polypeptide, and wherein the candidate compound structure defines a molecule having sufficient surface complementary to the RAGE polypeptide to specifically bind to the site on the RAGE polypeptide in an aqueous solution;
(d) assembling, by the computer, the subset of the chemical compound fragments of the candidate compound structure into a single compound structure; and
(e) synthesizing the single compound structure that binds to a site on a RAGE polypeptide so as to regulate RAGE-mediated cachetogenic activity.

2. The method of claim 1, further comprising the step of (f) assaying binding of the compound to a RAGE polypeptide in an in vitro, in vivo, or ex vivo assay.

3. The method of claim 2, further comprising the step of (g) assaying inhibition of cachexia or loss of myosin heavy chain by the compound in a functional cachexia assay.

4. The method of claim 1, wherein the structure of the candidate compound is designed de novo by assembling the subset of the chemical compound fragments of the chemical compound into a single compound structure.

5. The method of claim 3, further comprising the step of (h) modifying the candidate compound based upon the positioning, alignment, and interactions between the candidate compound and one or more amino acids comprising the site.

6. The method of claim 3, wherein the results of the assay of step (f) or step (g) provide further structure related binding information such that other candidate compounds are selected for evaluation.

7. The method of claim 1, wherein the candidate compound structure or the subset of the chemical compound fragments thereof are screened from a virtual compound library.

* * * * *

SEQUENCE LISTING

<160> NUMBER OF SEQ ID NOS: 10

<210> SEQ ID NO 1
<211> LENGTH: 237
<212> TYPE: PRT
<213> ORGANISM: Homo sapiens

<400> SEQUENCE: 1

Met Asp Leu Trp Ser Ala Gly Cys Val Phe Tyr Glu Ile Ala Ser Leu
1               5                   10                  15

Gln Pro Leu Phe Pro Gly Val Asn Glu Leu Asp Gln Ile Ser Lys Ile
            20                  25                  30

His Asp Val Ile Gly Thr Pro Ala Gln Lys Ile Leu Thr Lys Phe Lys
        35                  40                  45

Gln Ser Arg Ala Met Asn Phe Asp Phe Pro Phe Lys Lys Gly Ser Gly
    50                  55                  60

Ile Pro Leu Leu Thr Thr Asn Leu Ser Pro Gln Cys Leu Ser Leu Leu
65                  70                  75                  80

His Ala Met Val Ala Tyr Asp Pro Asp Glu Arg Ile Ala Ala His Gln
                85                  90                  95

Ala Leu Gln His Pro Tyr Phe Gln Glu Gln Arg Lys Thr Glu Lys Arg
            100                 105                 110

Ala Leu Gly Ser His Arg Lys Ala Gly Phe Pro Glu His Pro Val Ala
        115                 120                 125

Pro Glu Pro Leu Ser Asn Ser Cys Gln Ile Ser Lys Glu Gly Arg Lys
    130                 135                 140

Gln Lys Gln Ser Leu Lys Gln Glu Glu Asp Arg Pro Lys Arg Arg Gly
145                 150                 155                 160

Pro Ala Tyr Val Met Glu Leu Pro Lys Leu Lys Leu Ser Gly Val Val
                165                 170                 175

Arg Leu Ser Ser Tyr Ser Ser Pro Thr Leu Gln Ser Val Leu Gly Ser
            180                 185                 190

Gly Thr Asn Gly Arg Val Pro Val Leu Arg Pro Leu Lys Cys Ile Pro
        195                 200                 205

Ala Ser Lys Lys Thr Asp Pro Gln Lys Asp Leu Lys Pro Ala Pro Gln
    210                 215                 220

Gln Cys Arg Leu Pro Thr Ile Val Arg Lys Gly Gly Arg
225                 230                 235

<210> SEQ ID NO 2
<211> LENGTH: 1268
<212> TYPE: DNA
<213> ORGANISM: Homo sapiens

<400> SEQUENCE: 2
gccaggaccc tggaaggaag caggatggca gccggaacag cagttggagc ctgggtgctg      60
gtcctcagtc tgtgggggggc agtagtaggt gctcaaaaca tcacagcccg gattggcgag     120
ccactggtgc tgaagtgtaa gggggccccc aagaaaccac cccagcggct ggaatgcaaa     180
ctgaacacag gccggacaga agcttggaag gtcctgtctc cccagggagg aggcccctgg     240
gacagtgtgg ctcgtgtcct tcccaacggc tccctcttcc ttccggctgt cgggatccag     300
gatgagggga ttttccggtg ccaggcaatg aacaggaatg gaaaggagac caagtccaac     360
taccgagtcc gtgtctacca gattcctggg aagccagaaa ttgtagattc tgcctctgaa     420
ctcacggctg gtgttcccaa taaggtgggg acatgtgtgt cagagggaag ctaccctgca     480

```
gggactctta gctggcactt ggatgggaag ccctggtgc ctaatgagaa gggagtatct      540
gtgaaggaac agaccaggag acaccctgag acagggctct tcacactgca gtcggagcta      600
atggtgaccc cagcccgggg aggagatccc cgtcccacct tctcctgtag cttcagccca      660
ggccttcccc gacaccgggc cttgcgcaca gccccatcc agcccgtgt ctgggagcct       720
gtgcctctgg aggaggtcca attggtggtg gagccagaag gtggagcagt agctcctggt      780
ggaaccgtaa ccctgacctg tgaagtccct gcccagccct ctcctcaaat ccactggatg      840
aaggatggtg tgcccttgcc ccttccccc agccctgtgc tgatcctccc tgagataggg      900
cctcaggacc agggaaccta cagctgtgtg ccacccatt ccagccacgg gccccaggaa       960
agccgtgctg tcagcatcag catcatcgaa ccaggcgagg aggggccaac tgcaggctct     1020
gtggaggat cagggctggg aactctagcc ctggccctgg ggatcctggg aggcctgggg      1080
acagccgccc tgctcattgg ggtcatcttg tggcaaaggc ggcaacgccg aggagaggag     1140
aggaaggccc cagaaaacca ggaggaagag gaggagcgtg cagaactgaa tcagtcggag     1200
gaacctgagg caggcgagag tagtactgga gggccttgag gggcccacag acagatccca     1260
tccatcag                                                              1268

<210> SEQ ID NO 3
<211> LENGTH: 101
<212> TYPE: PRT
<213> ORGANISM: Homo sapiens

<400> SEQUENCE: 3

Met Ser Asn Thr Gln Ala Glu Arg Ser Ile Ile Gly Met Ile Asp Met
1               5                   10                  15

Phe His Lys Tyr Thr Arg Arg Asp Asp Lys Ile Glu Lys Pro Ser Leu
                20                  25                  30

Leu Thr Met Met Lys Glu Asn Phe Pro Asn Phe Leu Ser Ala Cys Asp
            35                  40                  45

Lys Lys Gly Thr Asn Tyr Leu Ala Asp Val Phe Glu Lys Lys Asp Lys
        50                  55                  60

Asn Glu Asp Lys Lys Ile Asp Phe Ser Glu Phe Leu Ser Leu Leu Gly
65                  70                  75                  80

Asp Ile Ala Thr Asp Tyr His Lys Gln Ser His Gly Ala Ala Pro Cys
                85                  90                  95

Ser Gly Gly Ser Gln
            100

<210> SEQ ID NO 4
<211> LENGTH: 450
<212> TYPE: DNA
<213> ORGANISM: Homo sapiens

<400> SEQUENCE: 4
gtccaaacac acacatctca ctcatccttc tactcgtgac gcttcccagc tctggctttt       60
tgaaagcaaa gatgagcaac actcaagctg agaggtccat aataggcatg atcgacatgt      120
ttcacaaata caccagacgt gatgacaaga ttgagaagcc aagcctgctg acgatgatga      180
aggagaactt ccccaacttc cttagtgcct gtgacaaaaa gggcacaaat tacctcgccg      240
atgtctttga gaaaaaggac aagaatgagg ataagaagat tgattttttct gagtttctgt      300
ccttgctggg agacatagcc acagactacc acaagcagag ccatggagca gcgcctgtt      360
ccggggggcag ccagtgaccc agccccacca atgggcctcc agagacccca ggaacaataa     420
```
aatgtcttct cccaccagaa aaaaaaaaaa                                          450

<210> SEQ ID NO 5
<211> LENGTH: 93
<212> TYPE: PRT
<213> ORGANISM: Homo sapiens

<400> SEQUENCE: 5

Met Leu Thr Glu Leu Glu Lys Ala Leu Asn Ser Ile Ile Asp Val Tyr
1               5                   10                  15

His Lys Tyr Ser Leu Ile Lys Gly Asn Phe His Ala Val Tyr Arg Asp
            20                  25                  30

Asp Leu Lys Lys Leu Leu Glu Thr Glu Cys Pro Gln Tyr Ile Arg Lys
        35                  40                  45

Lys Gly Ala Asp Val Trp Phe Lys Glu Leu Asp Ile Asn Thr Asp Gly
    50                  55                  60

Ala Val Asn Phe Gln Glu Phe Leu Ile Leu Val Ile Lys Met Gly Val
65                  70                  75                  80

Ala Ala His Lys Lys Ser His Glu Glu Ser His Lys Glu
                85                  90

<210> SEQ ID NO 6
<211> LENGTH: 532
<212> TYPE: DNA
<213> ORGANISM: Homo sapiens

<400> SEQUENCE: 6
gagaaaccag agactgtagc aactctggca gggagaagct gtctctgatg gcctgaagct      60
gtgggcagct ggccaagcct aaccgctata aaaggagct gcctctcagc cctgcatgtc     120
tcttgtcagc tgtctttcag aagacctggt ggggcaagtc cgtgggcatc atgttgaccg     180
agctggagaa agccttgaac tctatcatcg acgtctacca caagtactcc ctgataaagg     240
ggaatttcca tgccgtctac agggatgacc tgaagaaatt gctagagacc gagtgtcctc     300
agtatatcag gaaaaagggt gcagacgtct ggttcaaaga gttggatatc aacactgatg     360
gtgcagttaa cttccaggag ttcctcattc tggtgataaa gatgggcgtg gcagcccaca     420
aaaaaagcca tgaagaaagc cacaaagagt agctgagtta ctgggcccag aggctgggcc     480
cctggacatg tacctgcaga ataataaagt catcaatacc tcaaaaaaaa aa              532

<210> SEQ ID NO 7
<211> LENGTH: 114
<212> TYPE: PRT
<213> ORGANISM: Homo sapiens

<400> SEQUENCE: 7

Met Thr Cys Lys Met Ser Gln Leu Glu Arg Asn Ile Glu Thr Ile Ile
1               5                   10                  15

Asn Thr Phe His Gln Tyr Ser Val Lys Leu Gly His Pro Asp Thr Leu
            20                  25                  30

Asn Gln Gly Glu Phe Lys Glu Leu Val Arg Lys Asp Leu Gln Asn Phe
        35                  40                  45

Leu Lys Lys Glu Asn Lys Asn Glu Lys Val Ile Glu His Ile Met Glu
    50                  55                  60

Asp Leu Asp Thr Asn Ala Asp Lys Gln Leu Ser Phe Glu Glu Phe Ile
65                  70                  75                  80

Met Leu Met Ala Arg Leu Thr Trp Ala Ser His Glu Lys Met His Glu
                85                  90                  95

Gly Asp Glu Gly Pro Gly His His His Lys Pro Gly Leu Gly Glu Gly
            100                 105                 110

Thr Pro

<210> SEQ ID NO 8
<211> LENGTH: 587
<212> TYPE: DNA
<213> ORGANISM: Homo sapiens

<400> SEQUENCE: 8
aaacactctg tgtggctcct cggctttgac agagtgcaag acgatgactt gcaaaatgtc    60
gcagctggaa cgcaacatag agaccatcat caacaccttc accaatatact ctgtgaagct   120 ggggcaccca gacaccctga accagggga attcaaagag ctggtgcgaa agatctgca    180 aaatttctc aagaaggaga ataagaatga aaaggtcata gaacacatca tggaggacct    240
ggacacaaat gcagacaagc agctgagctt cgaggagttc atcatgctga tggcgaggct    300
aacctgggcc tcccacgaga gatgcacga gggtgacgag ggccctggcc accaccataa    360
gccaggcctc ggggagggca ccccctaaga ccacagtggc caagatcaca gtggccacgg    420
ccacggccac agtcatggtg gccacggcca cagccactaa tcaggaggcc aggccaccct    480
gcctctaccc aaccagggcc ccggggcctg ttatgtcaaa ctgtcttggc tgtgggcta    540 ggggctgggg ccaaataaag tctcttcctc caagtcaaaa aaaaaaa                  587

<210> SEQ ID NO 9
<211> LENGTH: 576
<212> TYPE: PRT
<213> ORGANISM: Homo sapiens

<400> SEQUENCE: 9

Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
        115                 120                 125

Ser Ala Ser Glu Leu Thr Ala Gly Val Pro Asn Lys Val Gly Thr Cys
    130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175

Thr Arg Arg His Pro Glu Thr Gly Leu Phe Thr Leu Gln Ser Glu Leu
            180                 185                 190

Met Val Thr Pro Ala Arg Gly Gly Asp Pro Arg Pro Thr Phe Ser Cys

```
            195                 200                 205
Ser Phe Ser Pro Gly Leu Pro Arg His Arg Ala Leu Arg Thr Ala Pro
210                 215                 220
Ile Gln Pro Arg Val Trp Glu Pro Val Pro Leu Glu Glu Val Gln Leu
225                 230                 235                 240
Val Val Glu Pro Glu Gly Gly Ala Val Ala Pro Gly Gly Thr Val Thr
                245                 250                 255
Leu Thr Cys Glu Val Pro Ala Gln Pro Ser Pro Gln Ile His Trp Met
            260                 265                 270
Lys Asp Gly Val Pro Leu Pro Leu Pro Pro Ser Pro Val Leu Ile Leu
        275                 280                 285
Pro Glu Ile Gly Pro Gln Asp Gln Gly Thr Tyr Ser Cys Val Ala Thr
    290                 295                 300
His Ser Ser His Gly Pro Gln Glu Ser Arg Ala Val Ser Ile Ser Ile
305                 310                 315                 320
Ile Glu Pro Gly Glu Glu Gly Pro Thr Ala Gly Ser Val Gly Gly Ser
                325                 330                 335
Gly Leu Gly Thr Leu Ala Leu Ala Pro Arg Gly Pro Thr Ile Lys Pro
                340                 345                 350
Cys Pro Pro Cys Lys Cys Pro Ala Pro Asn Leu Leu Gly Gly Pro Ser
            355                 360                 365
Val Phe Ile Phe Pro Pro Lys Ile Lys Asp Val Leu Met Ile Ser Leu
        370                 375                 380
Ser Pro Ile Val Thr Cys Val Val Val Asp Val Ser Glu Asp Asp Pro
385                 390                 395                 400
Asp Val Gln Ile Ser Trp Phe Val Asn Asn Val Glu Val His Thr Ala
                405                 410                 415
Gln Thr Gln Thr His Arg Glu Asp Tyr Asn Ser Thr Leu Arg Val Val
                420                 425                 430
Ser Ala Leu Pro Ile Gln His Gln Asp Trp Met Ser Gly Lys Glu Phe
            435                 440                 445
Lys Cys Lys Val Asn Asn Lys Asp Leu Pro Ala Pro Ile Glu Arg Thr
        450                 455                 460
Ile Ser Lys Pro Lys Gly Ser Val Arg Ala Pro Gln Val Tyr Val Leu
465                 470                 475                 480
Pro Pro Pro Glu Glu Glu Met Thr Lys Lys Gln Val Thr Leu Thr Cys
                485                 490                 495
Met Val Thr Asp Phe Met Pro Glu Asp Ile Tyr Val Glu Trp Thr Asn
            500                 505                 510
Asn Gly Lys Thr Glu Leu Asn Tyr Lys Asn Thr Glu Pro Val Leu Asp
        515                 520                 525
Ser Asp Gly Ser Tyr Phe Met Tyr Ser Lys Leu Arg Val Glu Lys Lys
    530                 535                 540
Asn Trp Val Glu Arg Asn Ser Tyr Ser Cys Ser Val Val His Glu Gly
545                 550                 555                 560
Leu His Asn His His Thr Thr Lys Ser Phe Ser Arg Thr Pro Gly Lys
                565                 570                 575

<210> SEQ ID NO 10
<211> LENGTH: 212
<212> TYPE: PRT
<213> ORGANISM: Homo sapiens

<400> SEQUENCE: 10
```

-continued

```
Gly Ala Met Ala Gln Asn Ile Thr Ala Arg Ile Gly Glu Pro Leu Val
1               5                   10                  15

Leu Lys Cys Lys Gly Ala Pro Lys Lys Pro Pro Gln Arg Leu Glu Trp
            20                  25                  30

Lys Leu Asn Thr Gly Arg Thr Glu Ala Trp Lys Val Leu Ser Pro Gln
            35                  40                  45

Gly Gly Gly Pro Trp Asp Ser Val Ala Arg Val Leu Pro Asn Gly Ser
    50                  55                  60

Leu Phe Leu Pro Ala Val Gly Ile Gln Asp Glu Gly Ile Phe Arg Cys
65                  70                  75                  80

Gln Ala Met Asn Arg Asn Gly Lys Glu Thr Lys Ser Asn Tyr Arg Val
            85                  90                  95

Arg Val Tyr Gln Ile Pro Gly Lys Pro Glu Ile Val Asp Ser Ala Ser
            100                 105                 110

Glu Leu Thr Ala Gly Val Pro Asn Lys Val Gly Thr Cys Val Ser Glu
            115                 120                 125

Gly Ser Tyr Pro Ala Gly Thr Leu Ser Trp His Leu Asp Gly Lys Pro
    130                 135                 140

Leu Val Pro Asn Glu Lys Gly Val Ser Val Lys Glu Gln Thr Arg Arg
145                 150                 155                 160

His Pro Glu Thr Gly Leu Phe Thr Leu Gln Ser Glu Leu Met Val Thr
            165                 170                 175

Pro Ala Arg Gly Gly Asp Pro Arg Pro Thr Phe Ser Cys Ser Phe Ser
            180                 185                 190

Pro Gly Leu Pro Arg His Arg Ala Leu Arg Thr Ala Pro Ile Gln Pro
            195                 200                 205

Arg Val Trp Glu
            210
```